US012776414B2

(12) United States Patent
Vakhnovetskaya et al.

(10) Patent No.: US 12,776,414 B2
(45) Date of Patent: Oct. 27, 2026

(54) CLINICAL SETTINGS SERVICE FOR MEDICAL APPLICATION

(71) Applicant: Align Technology, Inc., San Jose, CA (US)

(72) Inventors: Maria Vakhnovetskaya, Moscow (RU); Anton Egorov, Moscow (RU); Alexey Shatunov, Moscow (RU); Artem Nosenko, Reutov City (RU); Dmitriy Nikolaevich Pavlov, Naro-Fominsk (RU); Igor Kanel, Cary, NC (US); Rostislav Koryakov, Lyubertsy (RU); Sergey Prokopets, Ramenskoye (RU); Nilesh Kontamwar, Pune (IN); Nikolay Konovalov, Volzhskii (RU); Egor Sedov, Istra (RU)

(73) Assignee: Align Technology, Inc., San Jose, CA (US)

( * ) Notice: Subject to any disclaimer, the term of this patent is extended or adjusted under 35 U.S.C. 154(b) by 18 days.

(21) Appl. No.: 18/747,332

(22) Filed: Jun. 18, 2024

(65) Prior Publication Data

US 2025/0014745 A1 Jan. 9, 2025

Related U.S. Application Data

(60) Provisional application No. 63/607,288, filed on Dec. 7, 2023, provisional application No. 63/525,439, filed on Jul. 7, 2023.

(51) Int. Cl.

| | |
|---|---|
| ***G16H 40/67*** | (2018.01) |
| ***G16H 50/70*** | (2018.01) |
| *A61C 7/00* | (2006.01) |

(52) U.S. Cl.
CPC ............ *G16H 40/67* (2018.01); *G16H 50/70* (2018.01); *A61C 7/002* (2013.01)

(58) Field of Classification Search
None
See application file for complete search history.

(56) References Cited

U.S. PATENT DOCUMENTS

| | | | |
|---|---|---|---|
| 5,975,893 | A | 11/1999 | Chishti et al. |
| 6,227,850 | B1 | 5/2001 | Chishti et al. |
| 6,227,851 | B1 | 5/2001 | Chishti et al. |
| 6,299,440 | B1 | 10/2001 | Phan et al. |
| 6,318,994 | B1 | 11/2001 | Chishti et al. |
| 6,371,761 | B1 | 4/2002 | Cheang et al. |
| 6,386,878 | B1 | 5/2002 | Pavlovskaia et al. |

(Continued)

OTHER PUBLICATIONS

Loques et al ("Adaptation issues in software architectures of remote health care systems." Proceedings of the 2010 ICSE Workshop on Software Engineering in Health Care. 2010) (Year: 2010).*

*Primary Examiner* — Christopher B Tokarczyk
(74) *Attorney, Agent, or Firm* — Lowenstein Sandler LLP

(57) ABSTRACT

A system comprises a first computing device that is configured to receive, at a clinical settings service executing on the first computing device, a request for clinical settings for a patient case from a medical application executing on a second computing device. The computing device is further configured to determine clinical settings for the patient case, determine one or more clinical settings files for the patient case, and second the one or more clinical settings files to the second computing device.

19 Claims, 12 Drawing Sheets

(56) References Cited

U.S. PATENT DOCUMENTS

| | | | |
|---|---|---|---|
| 6,406,292 | B1 | 6/2002 | Chishti et al. |
| 6,409,504 | B1 | 6/2002 | Jones et al. |
| 6,457,972 | B1 | 10/2002 | Chishti et al. |
| 6,488,499 | B1 | 12/2002 | Miller |
| 6,514,074 | B1 | 2/2003 | Chishti et al. |
| 6,554,611 | B2 | 4/2003 | Chishti et al. |
| 6,582,229 | B1 | 6/2003 | Miller et al. |
| 6,602,070 | B2 | 8/2003 | Miller et al. |
| 6,621,491 | B1 | 9/2003 | Baumrind et al. |
| 6,688,886 | B2 | 2/2004 | Hughes et al. |
| 6,726,478 | B1 | 4/2004 | Isiderio et al. |
| 6,729,876 | B2 | 5/2004 | Chishti et al. |
| 6,739,869 | B1 | 5/2004 | Taub et al. |
| 6,767,208 | B2 | 7/2004 | Kaza |
| 6,783,360 | B2 | 8/2004 | Chishti |
| 7,040,896 | B2 | 5/2006 | Pavlovskaia et al. |
| 7,063,532 | B1 | 6/2006 | Jones et al. |
| 7,074,038 | B1 | 7/2006 | Miller |
| 7,074,039 | B2 | 7/2006 | Kopelman et al. |
| 7,077,647 | B2 | 7/2006 | Choi et al. |
| 7,108,508 | B2 | 9/2006 | Hedge et al. |
| 7,134,874 | B2 | 11/2006 | Chishti et al. |
| 7,156,661 | B2 | 1/2007 | Choi et al. |
| 7,160,107 | B2 | 1/2007 | Kopelman et al. |
| 7,241,142 | B2 | 7/2007 | Abolfathi et al. |
| 7,293,988 | B2 | 11/2007 | Wen |
| 7,357,634 | B2 | 4/2008 | Knopp |
| 7,555,403 | B2 | 6/2009 | Kopelman et al. |
| 7,637,740 | B2 | 12/2009 | Knopp |
| 7,689,398 | B2 | 3/2010 | Cheng et al. |
| 7,736,147 | B2 | 6/2010 | Kaza et al. |
| 7,746,339 | B2 | 6/2010 | Matov et al. |
| 7,844,356 | B2 | 11/2010 | Matov et al. |
| 7,844,429 | B2 | 11/2010 | Matov et al. |
| 7,865,259 | B2 | 1/2011 | Kuo et al. |
| 7,878,804 | B2 | 2/2011 | Korytov et al. |
| 7,880,751 | B2 | 2/2011 | Kuo et al. |
| 7,904,308 | B2 | 3/2011 | Arnone et al. |
| 7,930,189 | B2 | 4/2011 | Kuo |
| 7,942,672 | B2 | 5/2011 | Kuo |
| 7,970,627 | B2 | 6/2011 | Kuo et al. |
| 7,970,628 | B2 | 6/2011 | Kuo et al. |
| 8,038,444 | B2 | 10/2011 | Kitching et al. |
| 8,044,954 | B2 | 10/2011 | Kitching et al. |
| 8,075,306 | B2 | 12/2011 | Kitching et al. |
| 8,092,215 | B2 | 1/2012 | Stone-Collonge et al. |
| 8,099,268 | B2 | 1/2012 | Kitching et al. |
| 8,108,189 | B2 | 1/2012 | Chelnokov et al. |
| 8,126,726 | B2 | 2/2012 | Matov et al. |
| 8,260,591 | B2 | 9/2012 | Kass et al. |
| 8,275,180 | B2 | 9/2012 | Kuo |
| 8,401,826 | B2 | 3/2013 | Cheng et al. |
| 8,439,672 | B2 | 5/2013 | Matov et al. |
| 8,562,338 | B2 | 10/2013 | Kitching et al. |
| 8,591,225 | B2 | 11/2013 | Wu et al. |
| 8,788,285 | B2 | 7/2014 | Kuo |
| 8,843,381 | B2 | 9/2014 | Kuo et al. |
| 8,874,452 | B2 | 10/2014 | Kuo |
| 8,896,592 | B2 | 11/2014 | Boltunov et al. |
| 8,930,219 | B2 | 1/2015 | Trosien et al. |
| 9,037,439 | B2 | 5/2015 | Kuo et al. |
| 9,060,829 | B2 | 6/2015 | Sterental et al. |
| 9,125,709 | B2 | 9/2015 | Matty |
| 9,211,166 | B2 | 12/2015 | Kuo et al. |
| 9,220,580 | B2 | 12/2015 | Borovinskih et al. |
| 9,364,296 | B2 | 6/2016 | Kuo |
| 9,375,300 | B2 | 6/2016 | Matov et al. |
| 9,414,897 | B2 | 8/2016 | Wu et al. |
| 9,492,245 | B2 | 11/2016 | Sherwood et al. |
| 9,642,678 | B2 | 5/2017 | Kuo |
| 10,248,883 | B2 | 4/2019 | Borovinskih et al. |
| 10,342,638 | B2 | 7/2019 | Kitching et al. |
| 10,463,452 | B2 | 11/2019 | Matov et al. |
| 10,595,966 | B2 | 3/2020 | Carrier, Jr. et al. |
| 10,617,489 | B2 | 4/2020 | Grove et al. |
| 10,722,328 | B2 | 7/2020 | Velazquez et al. |
| 10,779,718 | B2 | 9/2020 | Meyer et al. |
| 10,792,127 | B2 | 10/2020 | Kopelman et al. |
| 10,835,349 | B2 | 11/2020 | Cramer et al. |
| 10,973,611 | B2 | 4/2021 | Pokotilov et al. |
| 10,996,813 | B2 | 5/2021 | Makarenkova et al. |
| 10,997,727 | B2 | 5/2021 | Xue et al. |
| 11,020,205 | B2 | 6/2021 | Li et al. |
| 11,020,206 | B2 | 6/2021 | Shi et al. |
| 11,026,766 | B2 | 6/2021 | Chekh et al. |
| 11,033,359 | B2 | 6/2021 | Velazquez et al. |
| 11,071,608 | B2 | 7/2021 | Derakhshan et al. |
| 11,096,763 | B2 | 8/2021 | Akopov et al. |
| 11,116,605 | B2 | 9/2021 | Nyukhtikov et al. |
| 11,147,652 | B2 | 10/2021 | Mason et al. |
| 11,151,753 | B2 | 10/2021 | Gao et al. |
| 11,154,381 | B2 | 10/2021 | Roschin et al. |
| 11,259,896 | B2 | 3/2022 | Matov et al. |
| 11,357,598 | B2 | 6/2022 | Cramer |
| 11,395,717 | B2 | 7/2022 | Yuryev et al. |
| 11,432,908 | B2 | 9/2022 | Kopelman et al. |
| 11,464,604 | B2 | 10/2022 | Makarenkova et al. |
| 11,478,334 | B2 | 10/2022 | Matov et al. |
| 11,484,389 | B2 | 11/2022 | Sterental et al. |
| 11,534,272 | B2 | 12/2022 | Li et al. |
| 11,553,988 | B2 | 1/2023 | Mednikov et al. |
| 11,633,268 | B2 | 4/2023 | Moalem et al. |
| 11,642,195 | B2 | 5/2023 | Gao et al. |
| 11,651,494 | B2 | 5/2023 | Brown et al. |
| 11,654,001 | B2 | 5/2023 | Roschin et al. |
| 11,707,344 | B2 | 7/2023 | Roschin et al. |
| 11,723,748 | B2 | 8/2023 | Li et al. |
| 11,810,271 | B2 | 11/2023 | Shi et al. |
| 11,850,111 | B2 | 12/2023 | Derakhshan et al. |
| 11,864,970 | B2 | 1/2024 | Shojaei et al. |
| 11,903,793 | B2 | 2/2024 | Cramer et al. |
| 11,978,547 | B2 | 5/2024 | Levin et al. |
| 12,023,216 | B2 | 7/2024 | Pimenov et al. |
| 12,048,604 | B2 | 7/2024 | Roschin et al. |
| 12,048,605 | B2 | 7/2024 | Farkash et al. |
| 12,076,207 | B2 | 9/2024 | Liu et al. |
| 12,090,020 | B2 | 9/2024 | Cramer |
| 12,106,845 | B2 | 10/2024 | Meyer et al. |
| 12,125,581 | B2 | 10/2024 | Slynko et al. |
| 12,193,905 | B2 | 1/2025 | Chekhonin et al. |
| 12,220,288 | B2 | 2/2025 | Chekh et al. |
| 2003/0008259 | A1 | 1/2003 | Kuo et al. |
| 2003/0143509 | A1 | 7/2003 | Kopelman et al. |
| 2003/0207227 | A1 | 11/2003 | Abolfathi |
| 2004/0137400 | A1 | 7/2004 | Chishti et al. |
| 2004/0152036 | A1 | 8/2004 | Abolfathi |
| 2004/0197728 | A1 | 10/2004 | Abolfathi et al. |
| 2004/0259049 | A1 | 12/2004 | Kopelman et al. |
| 2005/0182654 | A1 | 8/2005 | Abolfathi et al. |
| 2005/0244791 | A1 | 11/2005 | Davis et al. |
| 2006/0127836 | A1 | 6/2006 | Wen |
| 2006/0127852 | A1 | 6/2006 | Wen |
| 2006/0127854 | A1 | 6/2006 | Wen |
| 2006/0275731 | A1 | 12/2006 | Wen et al. |
| 2006/0275736 | A1 | 12/2006 | Wen et al. |
| 2008/0306724 | A1 | 12/2008 | Kitching et al. |
| 2010/0009308 | A1 | 1/2010 | Wen et al. |
| 2010/0068672 | A1 | 3/2010 | Arjomand et al. |
| 2010/0068676 | A1 | 3/2010 | Mason et al. |
| 2010/0092907 | A1 | 4/2010 | Knopp |
| 2010/0167243 | A1 | 7/2010 | Spiridonov et al. |
| 2013/0204599 | A1* | 8/2013 | Matov .................... G16H 50/50 703/11 |
| 2017/0273760 | A1 | 9/2017 | Morton et al. |
| 2017/0319861 | A1* | 11/2017 | Golden .............. A61N 1/37235 |
| 2022/0023002 | A1 | 1/2022 | Cramer et al. |
| 2022/0023008 | A1* | 1/2022 | Cramer ................ G06V 10/443 |
| 2022/0054232 | A1* | 2/2022 | Wen ....................... A61C 7/002 |
| 2022/0079714 | A1 | 3/2022 | Paraketsov et al. |
| 2022/0104920 | A1 | 4/2022 | Wang et al. |
| 2022/0165388 | A1 | 5/2022 | Chernov et al. |
| 2022/0262007 | A1 | 8/2022 | Cramer et al. |
| 2022/0378549 | A1 | 12/2022 | Blanco et al. |
| 2023/0008836 | A1 | 1/2023 | Yazykov et al. |

(56) References Cited

U.S. PATENT DOCUMENTS

| | | | |
|---|---|---|---|
| 2023/0056427 | A1 | 2/2023 | Blanco et al. |
| 2023/0190411 | A1 | 6/2023 | Chiu et al. |
| 2023/0225831 | A1 | 7/2023 | Cramer et al. |
| 2023/0263594 | A1 | 8/2023 | Lobsiger et al. |
| 2023/0301752 | A1 | 9/2023 | Wang et al. |
| 2023/0325558 | A1 | 10/2023 | Kukk et al. |
| 2023/0352150 | A1 | 11/2023 | Meyer et al. |
| 2023/0414323 | A1 | 12/2023 | Sun et al. |
| 2024/0033041 | A1 | 2/2024 | Chernov et al. |
| 2024/0033045 | A1 | 2/2024 | Tanugula et al. |
| 2024/0065807 | A1 | 2/2024 | Chang et al. |
| 2024/0087184 | A1 | 3/2024 | Gao et al. |
| 2024/0108436 | A1 | 4/2024 | Grebenkin et al. |
| 2024/0122463 | A1 | 4/2024 | Li et al. |
| 2024/0122677 | A1 | 4/2024 | Popov et al. |
| 2024/0131795 | A1 | 4/2024 | Li et al. |
| 2024/0144480 | A1 | 5/2024 | Seeber et al. |
| 2024/0177397 | A1 | 5/2024 | Li et al. |
| 2024/0185420 | A1 | 6/2024 | Cramer et al. |
| 2024/0185518 | A1 | 6/2024 | Seeber et al. |
| 2024/0189078 | A1 | 6/2024 | Cramer et al. |
| 2024/0197449 | A1 | 6/2024 | Stroganov et al. |
| 2024/0216106 | A1 | 7/2024 | Choi et al. |
| 2024/0257342 | A1 | 8/2024 | Semenov et al. |
| 2024/0277450 | A1 | 8/2024 | Sherstennikov et al. |
| 2024/0293200 | A1 | 9/2024 | Kirsanov et al. |

* cited by examiner

101

CLINICAL SETTINGS SERVICE FOR MEDICAL APPLICATION

RELATED APPLICATIONS

This patent application claims the benefit under 35 U.S.C. § 119(e) of U.S. Provisional Application No. 63/525,439, filed Jul. 7, 2023, and further claims the benefit under 35 U.S.C. § 119(e) of U.S. Provisional Application No. 63/607,288, filed Dec. 7, 2023, both of which are incorporated by reference herein.

TECHNICAL FIELD

Embodiments of the present disclosure relate to the field of medical software and, in particular, to a clinical settings service for a medical application.

BACKGROUND

Medical software such as that used to develop treatment plans for patients or perform treatments on the patients is regulated under a strict set of safety regulations. For example, software as a medical device (SaMD) is software that performs one or more medical functions, and is regulated by various agencies. Regulations for medical software may impose constraints on when a version of the software can be used on patients, on who can use the version of the software, and so on. Additionally, when medical software is modified, it is important to test the new modified version of the software before rolling it out for general use in case the new version of the software should have problems that could negatively impact patients. This includes changes made to the clinical settings in the medical software. Accordingly, traditionally when clinical settings of medical software are updated, a new version of the medical software is generated and then must be tested and approved before it can be used. This includes first uninstalling a stable version of the software from one or more computing devices and then installing the new version of the medical software. Uninstalling the old version of the medical software and then installing the new version of the medical software can take hours to perform. During such time the computing device is unavailable for use on patient cases, and technicians that use the computing device may be idle.

SUMMARY

In a first example implementation, a method comprises: receiving, by a clinical settings service executing on a first computing device, a request for clinical settings for a patient case from a medical application executing on a second computing device; determining clinical settings for the patient case; determining one or more clinical settings files for the patient case; and sending the one or more clinical settings files to the second computing device.

In a second example embodiment, a method comprises: opening a patient case in a medical application executing on a first computing device; sending, by the first computing device, a request for clinical settings for the patient case to a clinical settings service executing on a second computing device; receiving one or more clinical settings files from the clinical settings service; reading the clinical settings from the one or more clinical settings files; generating a treatment plan for the patient case, the treatment plan comprising the clinical settings; and storing the treatment plan.

In a third example implementation, a non-transitory computer readable medium comprises instructions that, when executed by the first computing device of the first or second example implementations, cause the first computing device to perform the operations of the first or second example implementations.

In a fourth example implementation, a system comprises the first computing device of the first or second example implementations, which is configured to perform the method of the first or second example implementations.

BRIEF DESCRIPTION OF THE DRAWINGS

Embodiments of the present disclosure are illustrated by way of example, and not by way of limitation, in the figures of the accompanying drawings.

DETAILED DESCRIPTION

Figure 1A:
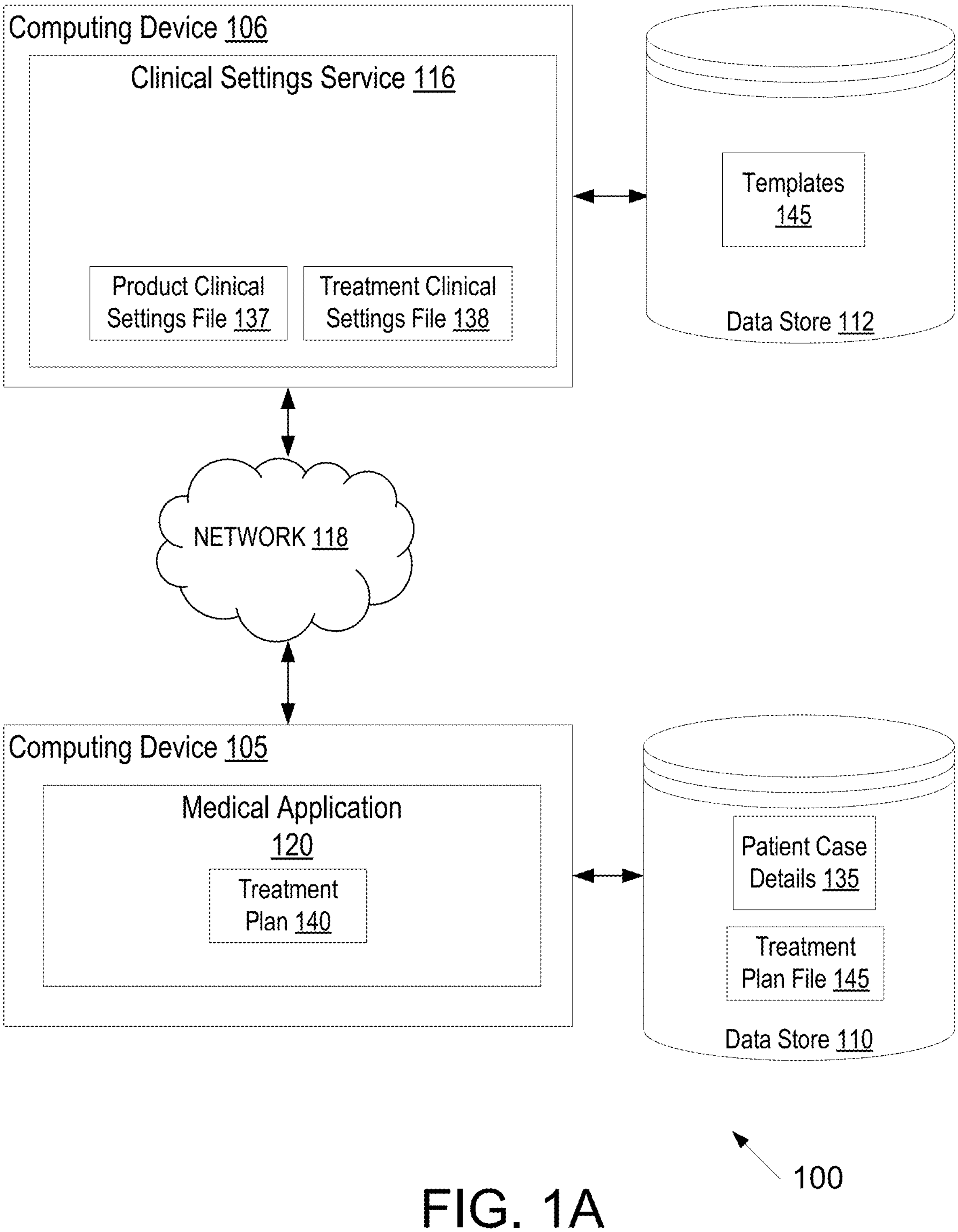
FIG. 1A illustrates one embodiment of a system for executing medical applications, in accordance with an embodiment.

Described herein are methods and systems for determining configuration settings for a medical application to apply in generation of a treatment plan for a patient case, in accordance with embodiments of the present disclosure. Embodiments cover a product configuration service for regional assessment and treatment planning of patients. Embodiments provide clinical parameter (settings) configuration and delivery capabilities. Embodiments enable the addition of completely new products based on clinical settings, existing in treatment planning software, addition and removal of clinical settings for products already used in production (e.g., clinical settings that already exist in treatment planning software), and the fine tuning of parameters of clinical settings for products already used in production. Embodiments also provide a dedicated process for delivering clinical settings for products. This makes the delivery process of clinical settings for products independent of medical application (e.g., treatment planning application) release cycles as well as making it easier and faster to deliver changes to product's clinical parameters. As used herein, a product may include a medical treatment type or option.

Medical applications and other medical software is subject to various regulations to ensure patient safety, data security, and the effectiveness of healthcare technology. Specific regulations vary based on country or region. In the United States (US), the Food and Drug Administration (FDA) regulates medical software under the Federal Food, Drug and Cosmetic Act (FD&C Act). Software that meets the definition of a medical device is subject to FDA oversight. Depending on the risk level, medical software may require premarket clearance (e.g., 510(k) clearance) or approval (e.g., Pre-market Approval—PMA) before it can be marketed. As new versions of the medical software are generated each time configuration settings of products offered by the medical software are modified, each such version may need to undergo rigorous testing before it can be released for general use in the US. Similarly, medical devices regulation (MDR) in the European Union provides regulations for medical devices, including software, within the European Union. Medical software must meet the requirements outlined in the MDR and may need to undergo conformity assessment procedures, such as certification by a notified body, based on the software's classification. Additionally, the International Medical Device Regulators Forum (IMDRF) is a global organization that harmonizes medical device regulations. The IMDF has released guidance documents related to software as a medical device (SaMD), providing recommendations on risk categorization, clinical evaluation, and cybersecurity. A commonality of each of the regulating bodies for medical applications/software is an imposition of additional rules and regulations for medical applications/software that do not exist for other types of applications/software.

Traditionally, in order to change the existing products (also referred to herein as treatment types or offerings) provided by a medical application or to add new product offerings to the medical application, one or more clinical settings is added or modified for those new or existing products in the medical application. Such changes to the medical application cause a new version of the medical application to be generated, which is then tested before the new version of the medical application can be deployed to and installed on computing devices used in production.

Software versioning is an important aspect of software development and maintenance, including medical software, to ensure traceability, transparency, and quality control. In order to ensure that changes made to medical applications/software as new versions of the medical applications/software are developed are safe and comply with the appropriate regulatory requirements, it is important that developers for medical applications/software to carefully manage the execution of different versions of the medical applications/software. The process for managing changes in medical software should be well-documented and followed consistently. This includes defining the criteria for releasing a new version, documenting the changes made in each version, and implementing a change control process to ensure proper review, approval, and validation of changes. Medical software developers should conduct risk assessments to identify potential risks associated with software changes and new versions. The risk assessment should consider factors such as the impact on patient safety, data integrity, and regulatory compliance. Each software version should undergo appropriate validation and verification processes to ensure that it performs as intended and meets the necessary requirements. This may include testing the software for functionality, performance, security, and compliance with relevant regulations.

Traditionally, as a new version of a medical application/software is generated, the new version of the medical application/software is installed on a small number of dedicated computing devices that do not have a stable production version of the medical application installed. This includes first uninstalling the production version of the software from those computing devices and then installing the new version of the medical application. Uninstalling the old version of the medical application and then installing the new version of the medical application can take hours to perform. Additionally, if the new version of the software ends up being problematic, then it must be uninstalled from the computing device before the old version of the software can be reinstalled, which again takes hours to perform. During such time the computing device is unavailable for use on patient cases, and technicians that use the computing device may be idle.

In embodiments, a clinical settings service (also referred to as a product settings service) is used to determine the clinical settings to apply for a treatment option for a patient case. The clinical settings service may be separate and distinct from medical applications that apply the determined clinical settings to generate treatment plans. By separating the management of clinical settings from the medical application and moving the clinical settings management to a remote service, the frequency with which new versions are developed for the medical application may be slowed down. Since the clinical settings determination is not part of the medical application, updates can be made to the clinical settings associated with one or more existing products and/or one or more new products without making any changes to the medical application. Since no changes are made to the medical application, a new version of the medical application does not need to be deployed and installed with changes to clinical settings of products each time changes are made to the clinical settings of the products. Additionally, or alternatively, the medical application may be subject to regulatory requirements, and updated approval of the medical application is not required with changes in the clinical settings since changes to the clinical settings do not constitute changes to the medical application. One or more of these factors can reduce the frequency of deploying, installing and testing new versions of medical applications. Instead, clinical settings themselves may be tested without impacting the medical application. Once clinical settings (e.g., for a new product or modified existing product) are successfully tested, those clinical settings may be stored to a template at the clinical settings service, and may be made generally available to the medical applications.

Embodiments provide a clinical settings service that may be a cloud-based service. The clinical settings service may receive requests for clinical settings from medical applications. Responsive to such a request, the clinical settings service may determine what clinical settings are appropriate for a particular patient case at hand based on data such as a region associated with the patient case, a doctor associated with the patient case, a product (e.g., treatment type) requested for the patient case, a patient type, and so on. The clinical settings service may retrieve or generate one or more clinical settings files based on the determined clinical settings, and may send the clinical settings file(s) to the requesting medical applications. The requesting medical applications may then apply the received clinical settings and generate a treatment plan, which may then be stored in the patient case.

Embodiments also cover systems and methods for adding new products and/or modifying existing products that are made available to medical applications via a clinical settings service. New products may be added and/or existing products may be modified simply by generating new clinical settings templates for those new and/or modified products. Clinical settings of the new and/or modified products may be tested, verified, and then deployed. Once the clinical settings of the new and/or modified products are deployed, those new and/or modified products are then available to the medical applications.

Embodiments are discussed with reference to medical applications. It should be understood that such embodiments also pertain to medical software other than medical applications. Accordingly, embodiments discussed herein apply to all types of medical software.

FIG. 1A illustrates one embodiment of a system 100 for using a clinical settings service 116 to provide clinical settings to a medical application 108, in accordance with an embodiment. In one embodiment, the system 100 includes a computing device 105, a data store 110, and a computing device 106. The computing devices 105, 106 may include physical machines and/or virtual machines hosted by physical machines. The physical machines may be rackmount servers, desktop computers, or other computing devices. The physical machines may include a processing device, memory, secondary storage, one or more input devices (e.g., such as a keyboard, mouse, tablet, speakers, or the like), one or more output devices (e.g., a display, a printer, etc.), and/or other hardware components. In one embodiment, one or more the computing device 105, 106 includes one or more virtual machines, which may be managed and provided by a cloud provider system. Each virtual machine offered by a cloud service provider may be hosted on one or more physical machine. Computing device 105 and computing device 106 may be connected by a network 118, which may include a local area network (LAN), a public wide area network (WAN) (e.g., the Internet), a private WAN (e.g., an intranet), or a combination thereof.

Computing device 105, 106 may be connected to a data store 110, 112 either directly or via a network. The network may be a local area network (LAN), a public wide area network (WAN) (e.g., the Internet), a private WAN (e.g., an intranet), or a combination thereof. Data store 110, 112 may be an internal data store, or an external data store that is connected to computing device 105 directly or via a network. Examples of network data stores include a storage area network (SAN), a network attached storage (NAS), and a storage service provided by a cloud provider system. Data store 110 may include one or more file systems, one or more databases, and/or other data storage arrangement.

In embodiments, computing device 105 includes a medical application 120. In one embodiment, medical application 120 is a dental and/or orthodontic treatment planning application. Medical application 120 may perform treatment planning, for example, for restorative dentistry and/or for orthodontics in some embodiments. The treatment planning application may be responsible for generating a treatment plan that includes a treatment outcome for a patient. The treatment plan may include and/or be based on an initial 2D and/or 3D image of a patient's dental arches. For example, the treatment planning application may receive 3D intraoral images (e.g., intraoral scans) of the patient's dental arches, and may stitch the 3D images or scans together to create a virtual 3D model of the dental arches. Alternatively, the treatment planning application may receive a virtual 3D model of a patient's dental arches. In embodiments, the treatment planning application receives a patient record 135 for a patient case, which may include, for example, intraoral scans, medical images, patient case details, 3D models of the patient's upper and/or lower dental arches, and so on.

The treatment planning application may then determine current positions and orientations of the patient's teeth from the virtual 3D model in the patient record 135 and determine target final positions and orientations for the patient's teeth represented as a treatment outcome. The treatment planning application may further determine one or more stages of treatment, and may determine target positions and orientations of the patient's teeth for each of the stages of treatment. The treatment planning application may additionally or alternatively determine one or more dental prosthetics to be used for a patient, such as a bridge, cap, crown, and so on.

With respect to orthodontic treatment, the treatment planning application may generate a virtual 3D model showing the patient's dental arches at the end of treatment as well as one or more virtual 3D models showing the patient's dental arches at various intermediate stages of treatment. Alternatively, or additionally, the treatment planning application may generate one or more 3D images and/or 2D images showing the patient's dental arches at various stages of treatment. The 3D models for any of the steps of treatment may be manipulated using a medical computer aided drafting (CAD) application in embodiments.

By way of non-limiting example, a dental treatment outcome may be the result of a variety of dental procedures. Such dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity, or a real or virtual model thereof, or directed to the design and preparation of the dental site to receive such a prosthesis. A prosthesis may include any restoration such as implants, crowns, veneers, inlays, onlays, and bridges, for example, and any other artificial partial or complete denture. The term orthodontic procedure refers, inter alia, to any procedure involving the oral cavity and directed to the design, manufacture or installation of orthodontic elements at a dental site within the oral cavity, or a real or virtual model thereof, or directed to the design and preparation of the dental site to receive such orthodontic elements. These elements may be appliances including but not limited to brackets and wires, retainers, clear aligners, or functional appliances. Any of treatment outcomes or updates to treatment outcomes described herein may be based on these orthodontic and/or dental procedures. Examples of orthodontic treatments are treatments that reposition the teeth, treatments such as mandibular advancement that manipulate the lower jaw, treatments such as palatal expansion that widen the upper and/or lower palate, and so on. For example, an update to a treatment outcome may be generated by interaction with a user to perform one or more procedures to one or more portions of a patient's dental arch or mouth.

A treatment plan for producing a particular treatment outcome may be generated by first generating an intraoral scan of a patient's oral cavity. From the intraoral scan a virtual 3D model of the upper and/or lower dental arches of the patient may be generated. A dental practitioner may then determine a desired final position and orientation for the patient's teeth on the upper and lower dental arches, for the patient's bite, and so on. This information may be used by the treatment planning application to generate a virtual 3D model of the patient's upper and/or lower arches after orthodontic treatment. This data may be used to create an orthodontic treatment plan. The orthodontic treatment plan may include a sequence of orthodontic treatment stages. Each orthodontic treatment stage may adjust the patient's dentition by a prescribed amount, and may be associated with a 3D model of the patient's dental arch that shows the patient's dentition at that treatment stage.

In some embodiments, the treatment planning application may receive or generate one or more virtual 3D models, virtual 2D models, 3D images, 2D images, or other treatment outcome models and/or images, which may be based on intraoral images or scans. For example, an intraoral scan of the patient's oral cavity may have been performed to generate an initial virtual 3D model of the upper and/or lower dental arches of the patient. The treatment planning application may then determine a final treatment outcome based on the initial virtual 3D model, and then generate a new virtual 3D model representing the final treatment outcome. The treatment planning application may additionally determine various intermediate stages of orthodontic treatment, and generate virtual 3D models of the patient's dental arches for each such intermediate stage. Clinically important factors such as an amount of force to be applied to teeth, an amount of rotation to be achieved by teeth, an amount of movement of teeth, teeth interactions, and so on should be considered by the treatment planning application in generation of the intermediate treatment stages.

Once a treatment plan is finalized, the various 3D models of the patient's dental arches for each of the stages of treatment may be used to manufacture orthodontic aligners for each of the stages of treatment. The patient may then wear the orthodontic aligners in order for treatment. At the end of treatment, the patient should have corrected dentition.

Medical application 120 may include default clinical settings for multiple different products (e.g., for multiple different types of treatments and/or different treatment options), for one or more regions, for one or more doctors, and so on. The default clinical settings may be clinical settings that were included in the medical application 120 at a time that a current version of the medical application 120 was developed or may have been provided by clinical settings service 116 after the current version of the medical application 120 was developed and deployed. The medical application 120 generally uses many clinical settings in the generation of a treatment plan 140. In some embodiments, medical application 120 uses default clinical settings to generate treatment plan 140 (e.g., if there is no current connection to clinical settings service 116 or clinical settings service 116 is otherwise unreachable). In some embodiments, medical application 120 relies on clinical settings service 116 to supply clinical settings to be used in the generation of a treatment plan 140. By separating the clinical settings management from medical application 120, a development cycle for products (e.g., medical treatments) that may be provided by medical application 120 may be separated from a development cycle for medical application 120. Such separation of the development cycle for medical products and the development cycle for medical application 120 may render the development cycle of medical products more efficient, may speed up the development cycle for medical products, may reduce regulatory overhead associated with medical application 120, and so on.

In embodiments, when medical application 120 is launched for a patient record 135 (e.g., a patient case), medical application 120 queries clinical settings service 116 to provide one or more clinical settings. The one or more clinical settings may be specific to a particular product (e.g., a particular medical treatment to be provided for a patient) in embodiments. In embodiments, medical application 120 may query clinical settings service 116 to determine what products are available, and may select one of the available products for treatment of the patient. In embodiments, medical application 120 may provide data to clinical settings service 116, which clinical settings service 116 may use to determine the clinical settings to provide to medical application for the patient case. The provided data may include, for example, a doctor identification, a region, a treatment type (e.g., a selected product), a patient type (e.g., one or more features of the patient), and so on, collectively referred to as patient case details 135 (e.g., which may be patient records or included in patient records). Patient type may include, for example, an adult patient, a teen patient, a child patient, a geriatric patient, a patient having certain medical conditions (e.g., high blood pressure), and so on. A region may include a geographic region, state and/or a country region. For example, a region may include U.S.A., California, Maryland, Minnesota, Europe, Germany, France, China, Australia, and so on. A treatment type may include, for example, orthodontic treatment of type 1 malocclusion, orthodontic treatment of type 2 malocclusion, orthodontic treatment of type 3 malocclusion, filling, bridge, cap, dentures, all-on-four treatment, and so on. One example of a treatment type is an orthodontic treatment type. Clinical settings for the orthodontic treatment type may include, for example, tooth movement settings.

In embodiments, clinical settings service 116 is a cloud-based service accessible via network 118, which may be a wide area network (WAN). Clinical settings service 116 may provide clinical settings to medical applications running in different doctor offices, in different geographical regions, in different countries, and so on. Different doctors may have their own preferences for medical treatments (e.g., for products), which may be saved in data store 112. Additionally, or alternatively, some doctors may have access to medical treatments that are not available to other doctors. For example, some doctors may have achieved certain certifications that indicate that those doctors are qualified to perform certain medical procedures or provide certain medical products. Accordingly, some doctors may have permissions for certain treatment types/options that other doctors do not have permissions for. Additionally, or alternatively, different countries may have different regulations with respect to medical treatments (e.g., products). Each of the doctor preferences, doctor permissions, country regulations, etc. may affect clinical settings to be used for a medical treatment and/or to be provided to medical application 120.

Clinical settings service 116 may use received data from a medical application 120 to determine appropriate clinical settings (e.g., clinical settings of a product) to be provided to medical application 120. The received data may include patient case details 135 such as treatment type, patient type, doctor identifier, region, and so on. In some embodiments, clinical settings service 116 receives a doctor identifier, patient type and/or region, and based on this information provides a list of available treatment types/options (e.g., of available products). A doctor may select one of the available treatment types/options, and the selected treatment type/option, the doctor identifier, the patient type and/or the region may be used to determine clinical settings to provide to medical application 120. In one embodiment, clinical settings service 116 generates one or more clinical settings files for a patient based on the provided patient case details (e.g., treatment type, patient type, doctor identifier, region, etc.). In one embodiment, clinical settings service 116 determines one or more templates 145 that are applicable to the received patient case details 135, and generates the clinical settings files using the determined templates 145. The templates 145 may include clinical settings associated with particular treatments, regions, doctors, patient types (e.g., adult vs. child, etc.), and so on.

The clinical settings may include user changeable clinical settings and user unchangeable clinical settings. In embodiments, user changeable clinical settings are included in a treatment clinical settings file 138 and user clinical settings not changeable by a user are included in a product clinical settings file 137. In some embodiments, product clinical settings file 137 and treatment clinical settings file 138 are JSON files. Alternatively, the product clinical settings file 137 and/or treatment clinical settings file 138 may have another file format, such as a text file format, an XML file format, a yet another markup language (YAML) format, etc. In some embodiments, the product clinical settings file 137 and the treatment clinical settings file 138 are pre-generated (e.g., as templates), and are retrieved by clinical settings service 116. In some embodiments, clinical settings service 116 generates the product clinical settings file 137 and treatment clinical settings file 138 responsive to receiving a request from medical application 120. For example, clinical settings service 116 may generate the product clinical settings file 137 and/or treatment clinical settings file 138 based on clinical settings included in one or more templates 145.

Clinical settings service 116 provides the determined clinical settings to medical application 120 in the form of one or more clinical settings files, which may include product clinical settings file 137 and treatment clinical settings file 138 in embodiments. In embodiments, product clinical settings file 137 and treatment clinical settings file 138 are specific for each product type and generated by a cloud-based product settings service. In embodiments, the treatment clinical settings file 138 contains settings that can be changed later by the user (e.g., by a computer aided drafting (CAD) designer during the treatment process, and the product clinical settings file 137 contains settings that are specific to the current product and that are unchangeable by the user (e.g., CAD designer).

Many different clinical settings may be provided, which may be dependent on a type of treatment to be performed, on a patient type, on a region, on a doctor, and so on. Some examples of clinical settings include movement limits (e.g., amount of tooth movement allowed between stages of treatment), rotation limits, force limits (e.g., amount of force allowed to be applied to teeth at stages of treatment), staging limits (e.g., a limit on the number of stages of treatment that are permitted), attachment details for attachments to be applied to teeth (e.g., type of attachments, placing of attachments, etc.), interproximal reduction (IPR) settings, whether to use elastics, where to apply elastics, palatal expansion settings, bite ramp settings, bite jump settings, distalizer settings, whether or not to allow overcorrection, whether or not to use passive treatment stages, whether and/or when to extract teeth, visualization settings (e.g., how to present information associated with the treatment plan to be generated), and so on. Many other clinical settings are also possible. Clinical settings may include parameters and associated values for those parameters. Parameters may be for any of the above indicated clinical settings and/or other clinical settings. Values may depend on a type of parameter or clinical setting. Some values may be true/false values, some values may be upper and/or lower limits, some values may be numeric values, some values may be text or ASCII values, and so on.

In embodiments, clinical settings service 116 may enable the addition of completely new products by combining clinical settings already introduced in treatment planning software. Clinical settings service 116 may provide a tool to add a new product, using clinical settings already introduced in treatment planning software, with full support for both manual and automated treatment planning systems. In embodiments, clinical settings service 116 may provide for pointed customization of the availability of certain clinical product settings for specific user groups (e.g., doctors, regions, etc.). In embodiments, clinical settings service 116 enables changing the configuration of clinical settings and clinical setting values for production products. Clinical settings service 116 may provide a tool to configure production products, such as by adding new clinical settings and/or removing or modifying existing clinical settings (e.g., changing the values of existing clinical settings) depending on criteria established by marketing (for example availability of dual arch passive aligners (DPA) in certain product types for certain regions or groups of doctors). In embodiments, clinical settings service 116 delivers any or all of the aforementioned clinical settings by a separate procedure which does not depend on a release cycle of the medical application 120 (e.g., of treatment planning software).

Medical application 120 may receive the clinical settings file(s) 137, 138, read the clinical settings information from the clinical settings file(s) 137, 138, and use the clinical settings information in generation of a treatment plan 140. The clinical settings file(s) 137, 138 may provide all of the settings for generation of a treatment plan for a particular medical product or treatment. Such settings may include constraints (e.g., upper and/or lower limits for one or more clinical settings), specific values for one or more clinical settings, availability or non-availability of one or more treatment options, visualization settings, and so on. In one embodiment, the clinical settings from the product clinical settings file 137 and from the treatment clinical settings file 138 are serialized, and a treatment plan file 145 that includes the serialized clinical settings is generated. Additional information may also be added to the treatment plan file, such as patient information (e.g., such as patient case details 135, 3D models of the patient's dental arches at one or more stages of treatment, etc.), doctor notes, and/or other relevant information is generated. The treatment plan file 145 may have a JSON file format, an XML file format, an Align data file (ADF) file format, or other file format.

The clinical settings (e.g., from product clinical settings file 137 and/or treatment clinical settings file 138) may be loaded by medical application 120 on receipt from clinical settings service 116. In embodiments, the clinical settings are loaded as an object or data structure in medical application 120. A generated treatment plan 140 may also be or include one or more objects and/or data structures. Such objects and/or data structures may not be in a format suitable for file storage.

Serialization is the process of converting an object or data structure into a format that can be easily stored or transmitted, and later reconstructed. Medical application 120 may serialize information into a file, which may include converting the in-memory representation of the data (such as an object, etc. of treatment plan 140) into a format that can be written to a file (e.g., a JSON file, an XML file, an ADF file, etc.). The treatment plan file 145 can then be transmitted and/or stored. The serialization process may preserve a state of the treatment plan 140 and/or clinical settings so that it can be retrieved and reloaded later. The treatment plan file 145 may later be loaded by medical application 120 or another medical application, and serialized information (e.g., serialized clinical settings) may be deserialized to reconstruct the information (e.g., to reconstruct the treatment plan 140, the clinical settings, etc.).

The treatment plan file 145 may then be stored to the data store 110. In one embodiment, the treatment plan file 145 is stored in a patient record (e.g., to the patient case). The treatment plan 140 and treatment plan file 145 may include information on an initial state of a patient's dentition, on planned states of the patient's dentition at one or more stages of treatment, information on the one or more stages of treatment, 3D models of the patient's dentition at one or more stages of treatment, 3D models of aligners to be used to correct the patient's dentition at one or more stages of treatment, information on whether, at which stages, and/or where to apply attachments, hooks, features, elastics, and so on. Later, the medical application 120 or another medical application may open the patient record, load the treatment plan, and review or update the treatment plan, which includes the previously determined clinical settings information.

When medical application 120 opens a patient case in embodiments, medical application 120 downloads from a cloud-based product settings file storage provided by clinical settings service 116 latest clinical settings file(s) 137, 138, specific for the case's product type, region and/or doctor, and applies settings from them to the patient case. Later, when the medical application 120 saves the patient case, medical application 120 may also save settings applied from clinical settings file(s) 137, 138 in the patient case itself. This provides usage of settings by downstream applications that will open the patient case (e.g., that will open the treatment plan file 145). In embodiments, medical application 120 (e.g., treatment planning software) contains default values for clinical settings which can be used in case of unavailability of clinical settings service 116, as described above.

Clinical settings service 116 may include or be associated with its own testing and approval process for new products, changes to clinical settings of existing produces, and so on. By separating the management of clinical settings from the medical application (e.g., treatment planning software), design control steps for changing clinical settings in the medical application may be skipped for the release cycle of the medical application. This may decrease delivery time of changes in clinical settings to a production environment. The clinical settings service 116 simplifies testing of any change in a product and product clinical settings by using collection of pre-prepared individual test cases for all clinical settings and running only a set of test cases for the clinical settings included in particular tested product rather than undergoing the standard approval process for new versions of medical applications in embodiments.

While FIG. 1A shows clinical settings service 116 providing clinical settings information for a single medical application, clinical settings service 116 may provide tailored clinical settings information for multiple different medical applications and/or multiple different instances of the same medical application. The different medical applications may execute on different computing devices, be located at different locations (e.g., in different geographic and/or political regions), etc.

Figure 1B:
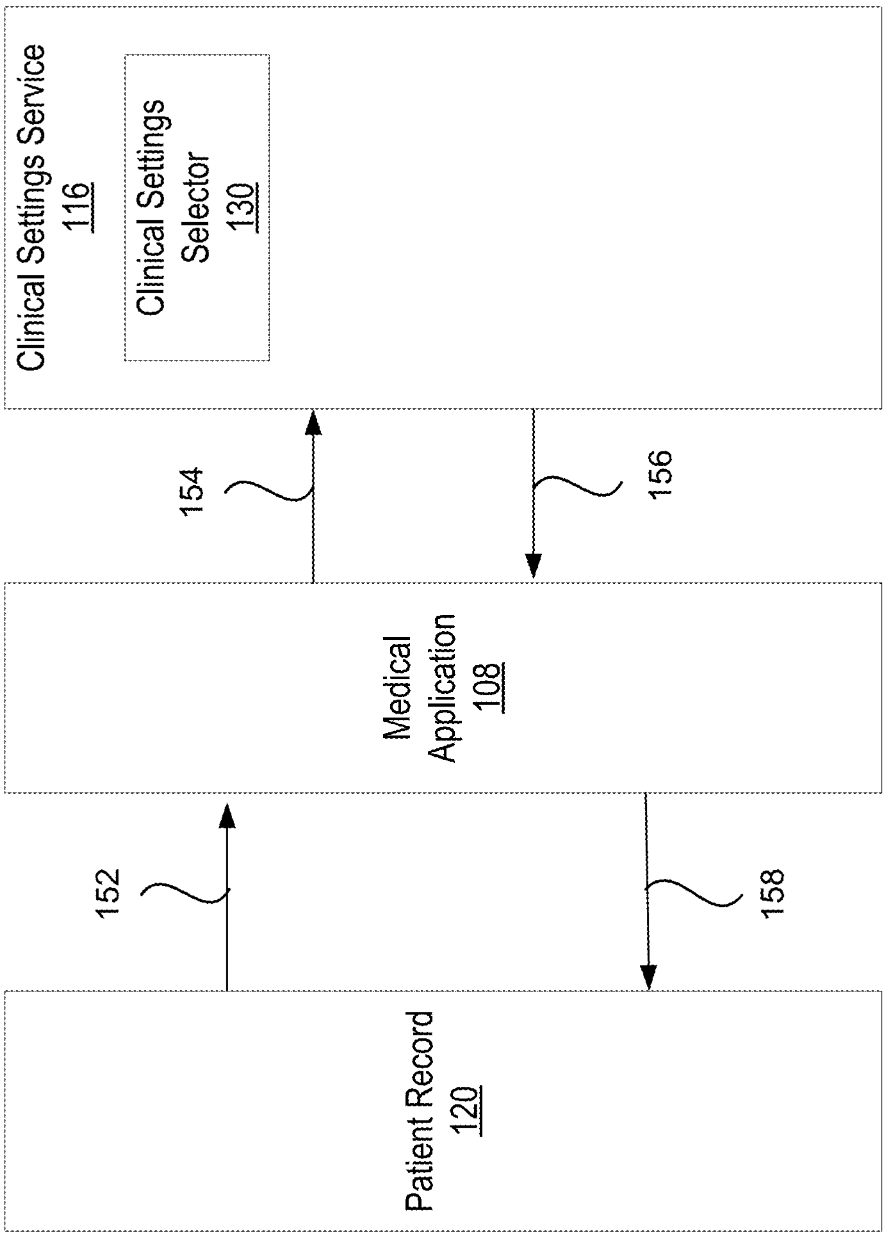
FIG. 1B illustrates one embodiment of determining and/or generating clinical settings files for a medical application, in accordance with an embodiment.

FIG. 1B illustrates one embodiment of a system 101 for determining and/or generating clinical settings files for a medical application 108, in accordance with an embodiment. As shown, a medical application 108 retrieves a patient record 120 for a particular patient case at operation 152. The medical application 108 then sends a request for clinical settings to a clinical settings service 116 at operation 154. The request may include patient case details, such as a patient type, a doctor identifier, a region identifier, a treatment type, and so on. A clinical settings selector 130 of the clinical settings service 116 determines clinical settings to apply for the patient case, and clinical settings service 116 provides the determined clinical settings to medical application 108 at operation 156. The medical application 108 generates a treatment plan based at least in part on the received clinical settings and information from the patient record 120, and then may store the treatment plan to the patient record 120 at operation 158.

FIGS. 2-11 below describe methods associated with a clinical settings service, in accordance with embodiments of the present disclosure. The methods depicted in FIGS. 2-11 may be performed by a processing logic that may comprise hardware (e.g., circuitry, dedicated logic, programmable logic, microcode, etc.), software (e.g., instructions run on a processing device), or a combination thereof. Various embodiments may be performed by a computing device 105 and/or computing device 106 as described with reference to FIG. 1A. In embodiments, some operations are performed on computing device 105 and some operations are performed on computing device 106.

Figure 2:
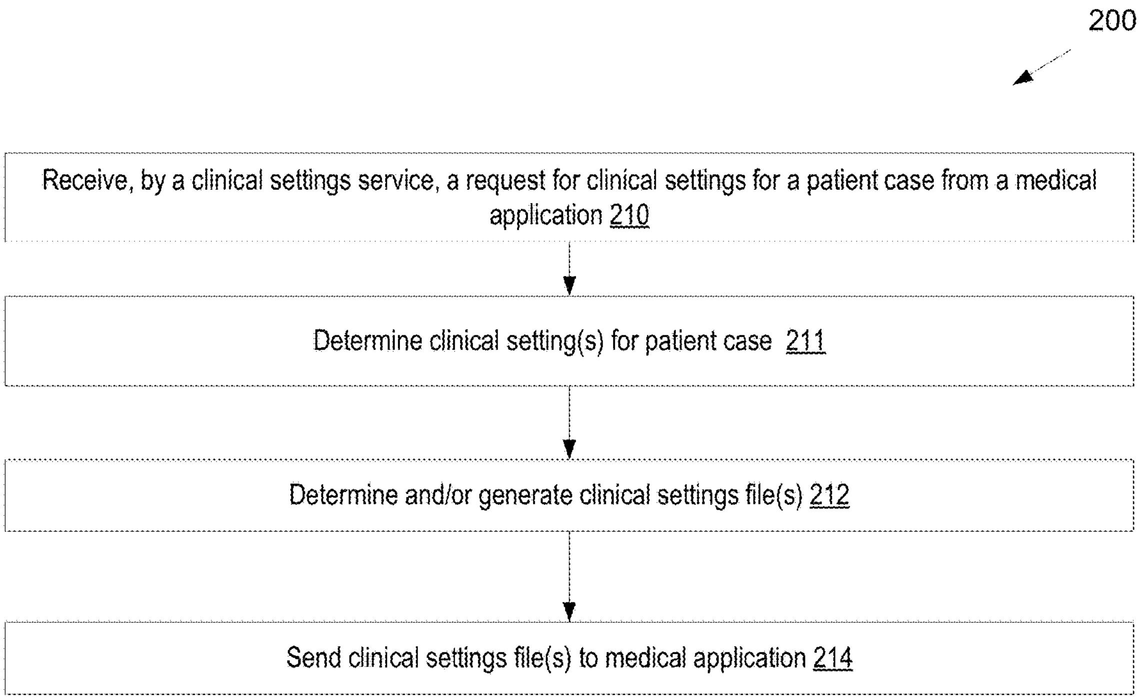
FIG. 2 illustrates a flow diagram for a method of determining and/or generating clinical settings files, in accordance with an embodiment.

FIG. 2 illustrates a flow diagram for a method 200 of determining and/or generating clinical settings files, in accordance with an embodiment. At block 210 of method 200, a clinical settings service receives a request for clinical settings for a patient case from a medical application. The request may include patient case details, such as a treatment type, a patient type, a doctor identifier, a region identifier, and so on. At block 211, the clinical settings service determines one or more clinical settings for the patient case. The clinical settings may be determined by performing a lookup on a set of stored clinical settings templates. Each of the clinical settings templates may be associated with one or more treatment types (e.g., one or more products), one or more patient types, one or more regions, one or more doctors, and so on. The clinical settings service may identify one or multiple clinical settings templates that correspond to one or more of the provided patient case details. The clinical settings service may then determine clinical settings from the one or multiple identified clinical settings templates.

At block 212, the clinical settings service determines and/or generates one or more clinical settings files having the determined clinical settings. At block 214, the clinical settings service sends the generated/determined clinical settings file(s) to the medical application. The medical application may then use the received clinical settings file(s) in generation of a treatment plan for the patient case.

In embodiments, products that are available to medical applications may be added and/or modified without making any changes to the medical applications. For example, products may be added by adding new clinical settings for new products (e.g., new medical treatments or medical treatment options) to a clinical settings services. In another embodiment, existing products may be modified by adjusting clinical settings for those products at a clinical settings service. In some embodiments, new products are added by adding new clinical settings templates for those new products to a clinical settings service. In some embodiments, existing products are modified by modifying one or more existing clinical settings templates for those products at the clinical settings service.

Figure 3:
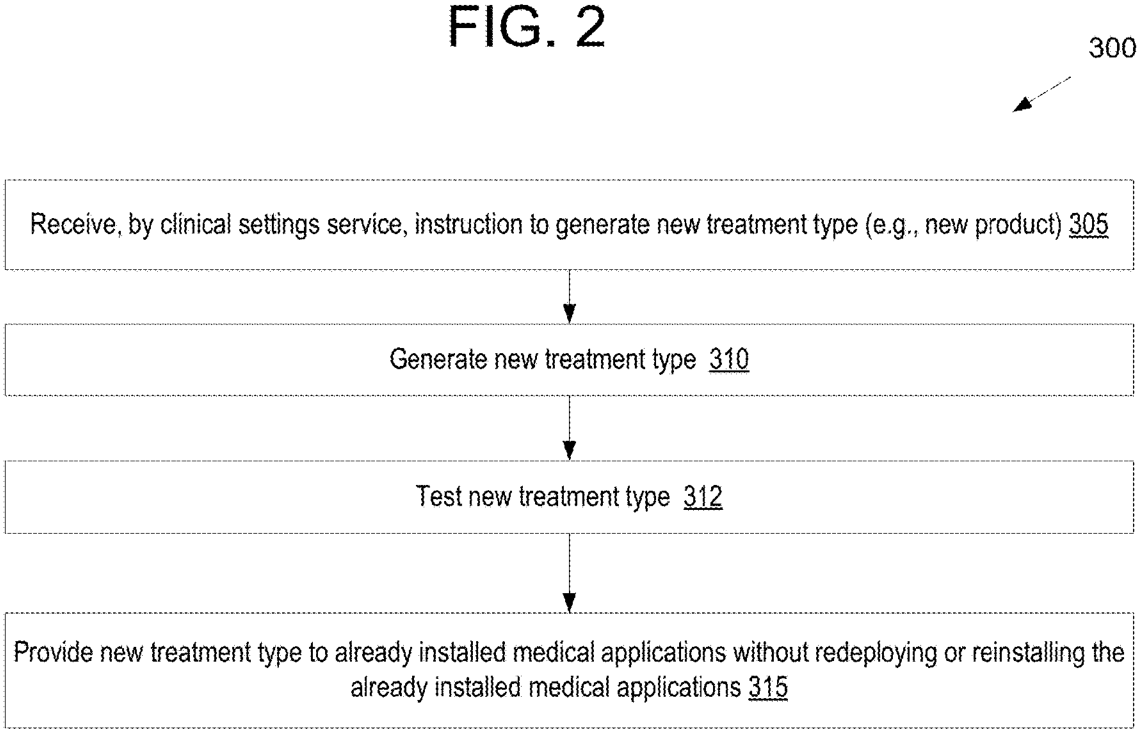
FIG. 3 illustrates a flow diagram for a method of updating a clinical settings service to cause the clinical settings service to support a new treatment type or product, in accordance with an embodiment.

FIG. 3 illustrates a flow diagram for a method 300 of updating a clinical settings service to cause the clinical settings service to support a new treatment type or product, in accordance with an embodiment. At block 305 of method 300, the clinical settings service receives an instruction to generate a new treatment type (e.g., a new product). The instructions may include parameters for clinical settings associated with the new treatment type, prior to receiving the request for clinical settings for the patient case. At block 310, the clinical settings service generates the new treatment type. Generating the new treatment type may include generating one or more clinical settings templates for the new treatment type. A user may provide a set of clinical settings to be used for the new treatment type, which may be stored in the one or more clinical settings templates. In some embodiments, the clinical settings service provides a user interface (e.g., a graphical user interface) that a user may interact with to select clinical settings to be used for the new treatment type. In some embodiments, the selected clinical settings may individually correspond to clinical settings that were already available to medical applications, but that may not have been applied in the particular arrangement of the new treatment type. Accordingly, the medical applications may already support each of the clinical settings of the new treatment type even though that new treatment type was not previously available on the medical applications.

At block 312, one or more tests may be performed on the new treatment type. The number and/or type of tests to perform may depend on the new treatment type, operations and/or parameters of the new treatment type, whether those operations and/or parameters have already been tested for other treatment type, and/or other information. A new treatment type may include options for one or more of an attachments delay, one or more tooth movement limits, one or more user interface (UI) elements, IPR, overcorrection, passive aligners, pontics, power arms, precision cuts, staging limits, bite ramps, and so on. Different tests may be performed for different features in some embodiments. The tests for a new treatment type may be the same as, or different from, tests for modifications to existing treatment types in embodiments. A few example test sequences are provided below, which may be applied to new treatment types and/or modifications to existing treatment types.

In one embodiment, testing an attachments delay option includes performing the following operations:

1) Place all files for new (or existing) treatment type in a same directory, and confirm that are files are so placed;
2) Open a case in a medical application with the new treatment type, and confirm that the case has been opened without the medical application crashing, without unexpected messages (e.g., any messages not indicated in a test scenario), without unexpected windows and/or plugins (e.g., any windows and/or plugins not indicated in the test scenario), and confirm that a scene for the case is shown in a graphical user interface of the medical application without any distortions;
3) Determine that expected treatment features are available in a treatment features schedule;
4) Select a treatment stage at which to start using attachments to teeth;
5) Optionally determine placement of ridges and/or attachments to one or more teeth on upper and/or lower dental arches;
6) Save and close file(s), and determine that scene stops showing, no crashes or exceptions occur, a saved file size is greater than 0 kB, and that no duplicate files are generated.

In one embodiment, testing a tooth movement limit includes performing the following operations:

1) Place all files for new (or existing) treatment type in a same directory, and confirm that are files are so placed;
2) Open a case in a medical application with the new treatment type, and confirm that the case has been opened without the medical application crashing, without unexpected messages (e.g., any messages not indicated in a test scenario), without unexpected windows and/or plugins (e.g., any windows and/or plugins not indicated in the test scenario), and confirm that a scene for the case is shown in a graphical user interface of the medical application without any distortions;
3) Determine a final position/orientation of a patient's teeth;
4) Assess a difficulty of the patient case, and provide difficultly assessment in the GUI;
5) Save and close file(s), and determine that scene stops showing, no crashes or exceptions occur, a saved file size is greater than 0 kB, and that no duplicate files are generated.

In one embodiment, testing UI elements includes performing the following operations:

1) Place all files for new (or existing) treatment type in a same directory, and confirm that are files are so placed;
2) Open a case in a medical application with the new treatment type, and confirm that the case has been opened without the medical application crashing, without unexpected messages (e.g., any messages not indicated in a test scenario), without unexpected windows and/or plugins (e.g., any windows and/or plugins not indicated in the test scenario), and confirm that a scene for the case is shown in a graphical user interface of the medical application without any distortions;
3) Confirm that correct product name is displayed, and that correct text and/or colors are used in a status bar;
4) Save and close file(s), and determine that scene stops showing, no crashes or exceptions occur, a saved file size is greater than 0 kB, and that no duplicate files are generated.

At block 315, the clinical settings service may provide the new treatment type to already installed medical applications without redeploying or reinstalling those already installed medical applications (e.g., once the new treatment type has passed the one or more tests at block 312). Accordingly, new treatment types (e.g., products) may be added to medical applications without updating those applications, which greatly speeds up the introduction of new products.

Figure 4:
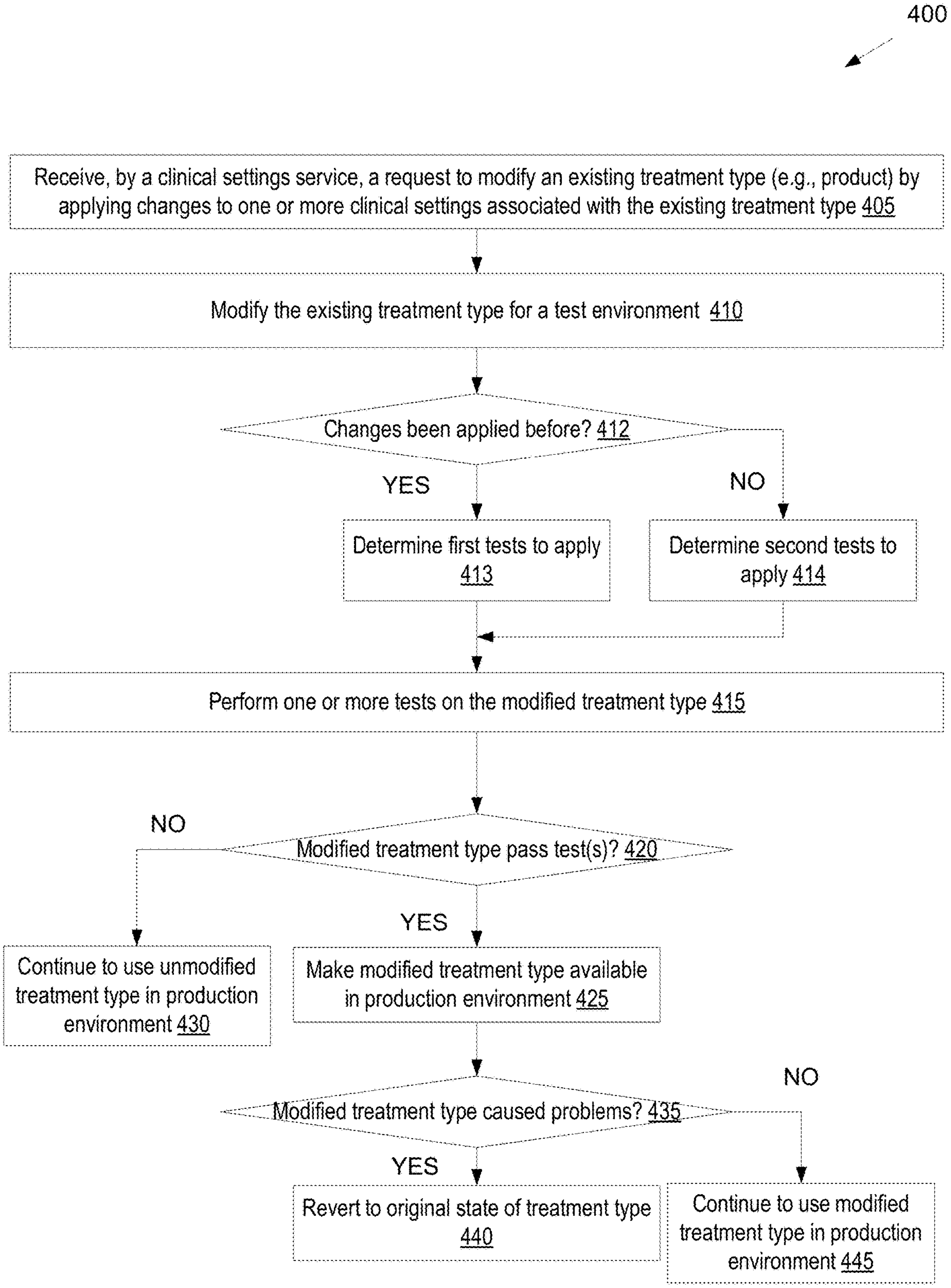
FIG. 4 illustrates a flow diagram for a method of modifying one or more products of a clinical settings service, in accordance with an embodiment.

FIG. 4 illustrates a flow diagram for a method 400 of modifying one or more products of a clinical settings service, in accordance with an embodiment. At block 405 of method 400, a clinical settings service receives a request to modify an existing treatment type (e.g., an existing product). The request may include instructions to modify or change one or more clinical settings associated with the existing treatment type. In embodiments, the request is received via a user interface (e.g., a graphical user interface) of the clinical settings service. For example, a user may request that data for an existing treatment type be shown and/or loaded. The various clinical settings may be displayed, and the user may select one or more of the clinical settings, and indicate adjustments to those clinical settings. For example, the user may type in new values for one or more clinical settings, may adjust a slider for the one or more settings, may click on one or more true/false or on/off buttons for the one or more settings, and so on.

At block 410, the clinical settings service modifies the existing treatment type in accordance with the request. The existing treatment may be modified for a test environment for testing. During this time, the original version of the clinical settings for the treatment type may be maintained and used for a production environment.

At block 412, the clinical settings service may determine whether the applied changes have been applied previously (e.g., in one or more prior versions of the clinical settings for the product). If the changes to the clinical settings have already been applied, then the changes may be classified as simple changes. Accordingly, the method may proceed to block 413 and one or more first tests may be performed. If the changes to the clinical settings have not been applied in the past, then the changes may be classified as complex changes. Accordingly, the method may proceed to block 414 and one or more second tests may be performed. The one or more second tests may be more extensive than the one or more first tests. Additionally, or alternatively, a body that reviews results of the one or more second tests may be different from a body that reviews results of the one or more first tests.

At block 415, processing logic performs one or more tests on the modified treatment type in accordance with the first tests determined at block 413 or the second tests determined at block 414. The tests may be based at least in part on options for one or more of an attachments delay, one or more tooth movement limits, one or more user interface (UI) elements, IPR, overcorrection, passive aligners, pontics, power arms, precision cuts, staging limits, bite ramps, and so on. Different tests may be performed for different features in some embodiments. The tests for new treatment type may be the same as, or different from, tests for modifications to existing treatment types in embodiments.

At block 420, processing logic determines whether the modified treatment type passes all tests. If the modified treatment type fails to pass one or more tests, then at block 430 a previous version of the treatment type may continue to be used in a production environment. If at block 420 a determination is made that the modified treatment type does pass all tests, the method continues to block 425. At block 425, processing logic makes the modified treatment type available in the production environment. The modified treatment type may replace the original version of the treatment type, or may be provided as an alternative option of the original version of the treatment type in embodiments.

After a modified treatment type has been released to the production environment, continued monitoring of cases that apply the modified treatment type may be observed. Each such case may be assessed to determine if there are any problems that were introduced by the modified treatment type (e.g., which may not have occurred for the previous version of the treatment type). If any such errors are observed, then the method may continue to block 440. If no such errors are observed, then the method may continue to block 445.

At block 440, processing logic reverts the treatment type to the original state of the treatment type. At block 445, processing logic continues to use the modified treatment type in the production environment.

Figure 5:
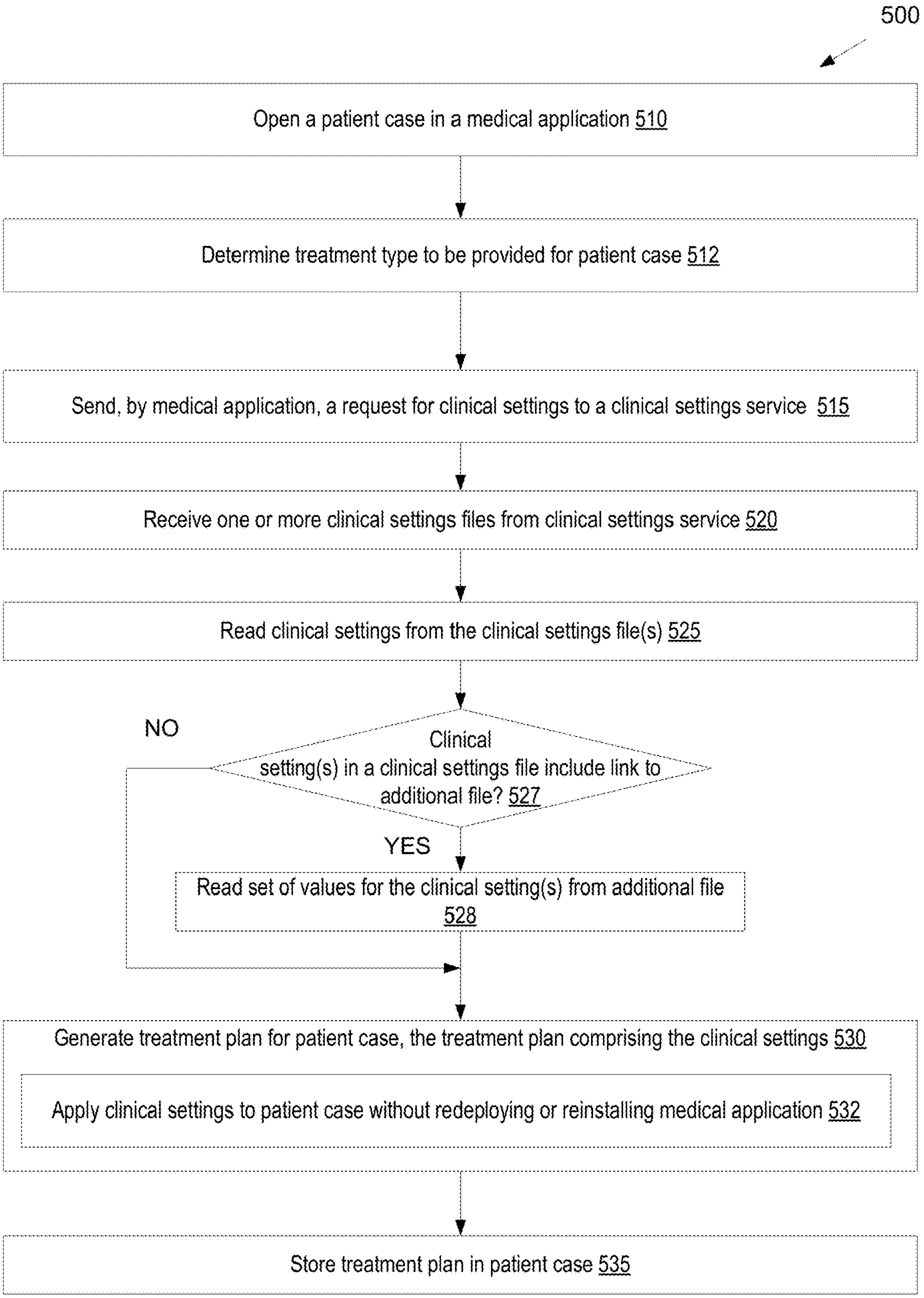
FIG. 5 illustrates a flow diagram for a method of obtaining clinical settings from a clinical settings service to generate a treatment plan for a patient, in accordance with an embodiment.

FIG. 5 illustrates a flow diagram for a method 500 of obtaining clinical settings from a clinical settings service to generate a treatment plan for a patient, in accordance with an embodiment. In embodiments, method 500 may be performed by a computing device of a doctor (e.g., a computing device in a doctor office, or a computing device accessed by a doctor). For example, method 500 may be executed by computing device 105 of FIG. 1A in embodiments.

At block 510 of method 500, a patient case may be opened in a medical application executing on a computing device. In an example, the medical application is an orthodontic treatment planning application. At block 512, processing logic determines a treatment type (e.g., a medical product) to be provided for the patient case. The medical application may provide a list of optional treatment types (also referred to simply as treatments). In some embodiments, prior to providing a list of available treatment types, the medical application queries a clinical settings service, which may provide an updated list of treatment options to the medical application. The query to the clinical settings service may include one or more patient case details, such as a doctor identifier, a region identifier, a patient type, and so on. Different treatments may be available for different doctors, for different regions, for different patient types (e.g., for children, teens, adults, geriatrics, etc.), and so on. Accordingly, the list of available treatments may depend on the patient case details in some instances.

At block 515, the medical application sends a request for clinical settings to the clinical settings service. The request may include a selection of a treatment type and one or more patient case details, such as patient type, region, doctor identifier, and so on. At block 520, the medical application receives one or more clinical settings files from the clinical settings service.

At block 527, the medical application reads clinical settings from the one or more received clinical settings files. Some clinical settings files may include all clinical settings encoded therein. Other clinical settings files may include links to further clinical settings files that include further clinical settings. For example, some types of clinical settings, such as tooth movement restrictions, include an array of values. For example, there may be different tooth movement restrictions for different teeth, for different directions, for rotations about different axes, and so on. Such tooth movement restrictions may be represented in an array of tooth movement restrictions in some embodiments. Rather than include such an array of tooth movement restrictions in a clinical settings file, the clinical settings file may include a link to an additional clinical settings file that includes the array of tooth movement restrictions. In an embodiment, the link has a yet another markup language (YAML) format. YAML is a human-readable data serialization standard.

If the medical application determines that the clinical settings file(s) include one or more links to other files, the method continues to block 528. If the medical application determines that the clinical settings file(s) do not include any links to other files, the method proceeds to block 530. At block 528, processing logic reads a set of values for one or more of the clinical settings from the additional file(s) using the link(s) included in the other clinical settings file(s).

At block 530, the medical application generates a treatment plan for the patient case. The generated treatment plan includes the clinical settings provided by the clinical settings service. This may include at block 532 applying the clinical settings to the patient case without redeploying or reinstalling the medical application even in instances where the clinical settings for the treatment to be performed (and even where the treatment to be performed) were not available when the medical application was deployed or installed. At block 535, the treatment plan may be stored in the patient case (e.g., patient record). This may include serializing information in the treatment plan, such as serializing the clinical settings.

Figure 6:
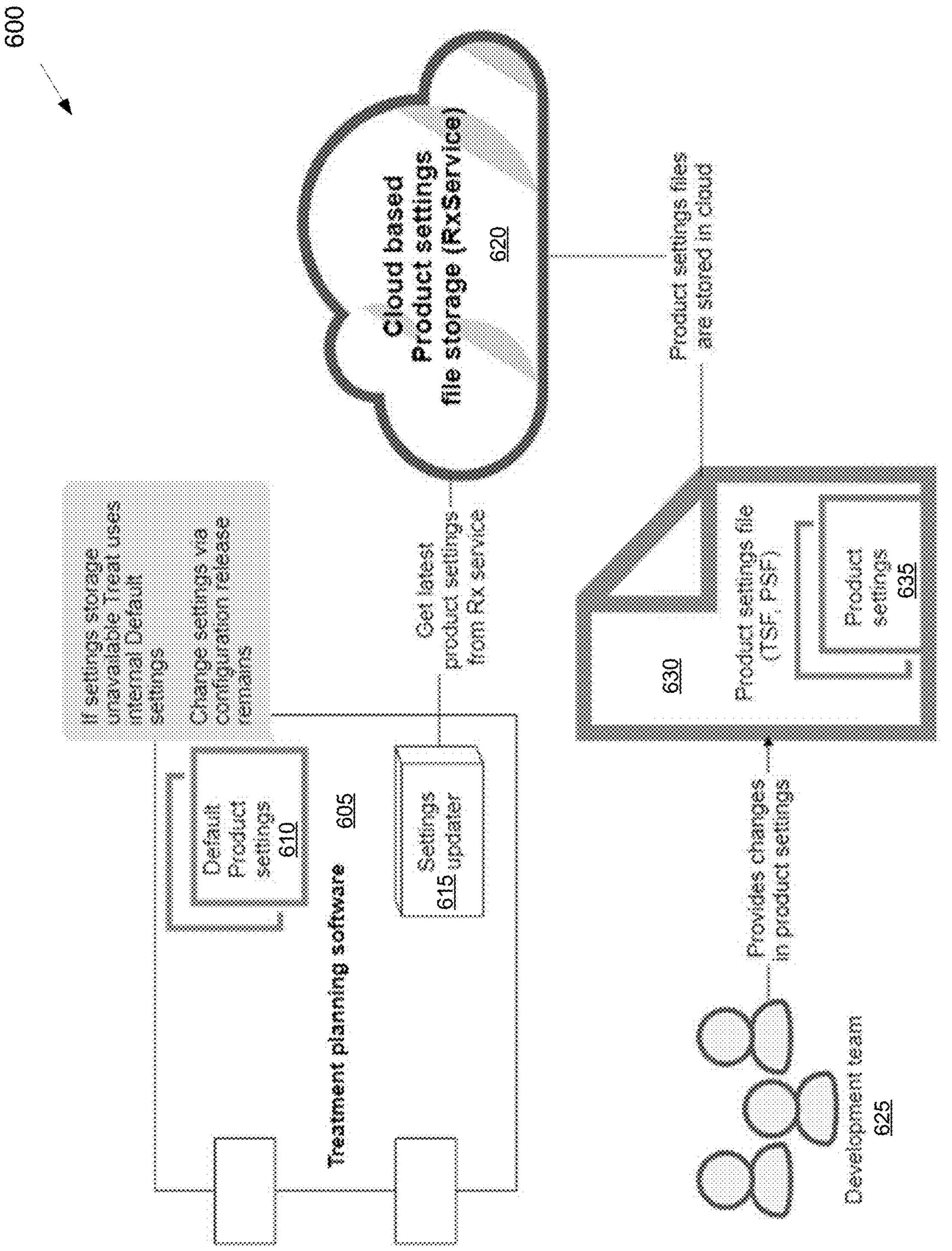
FIG. 6 illustrates a diagram for a method of implementing a clinical settings service, in accordance with an embodiment.

FIG. 6 illustrates a diagram for a method 600 of implementing a clinical settings service, in accordance with an embodiment. At block 625 of method 600, a development team 625 may provide changes to product settings for one or more products (e.g., for one or more treatment types or treatments). Based on the provided changes, one or more clinical settings files (e.g., a product settings file PSF and/or treatment settings file (TSF)) 630 may be generated, each containing one or more clinical settings (also referred to as product settings) 635. In some instances, multiple different versions of the clinical settings files 630 may be generated. For example, different versions of the clinical settings files 630 may be pre-generated for different doctors, for different regions, and so on. In some embodiments, clinical settings templates are generated, which may be used to later generate patient-specific clinical settings files. The generated clinical settings files 630 may be stored in a cloud-based product settings file storage (e.g., a prescription service or clinical settings service) 620.

A doctor may execute treatment planning software 605 for a patient case. The treatment planning software 605 may load a patient case. When the treatment planning software is loaded, when the patient case is loaded, and/or at a later time a settings updater 615 of the treatment planning software 605 may generate a query for clinical settings from the cloud-based product settings file storage or clinical settings service 620. The query from the treatment planning software may or may not include patient case details for the patient case. The cloud-based product settings file storage and/or clinical settings service 620 may generate and/or retrieve appropriate clinical settings file(s), and return the clinical settings file(s) to treatment planning software 605. Treatment planning software 605 may then proceed to design a treatment plan for the patient case using the received clinical settings files 630.

Figure 7:
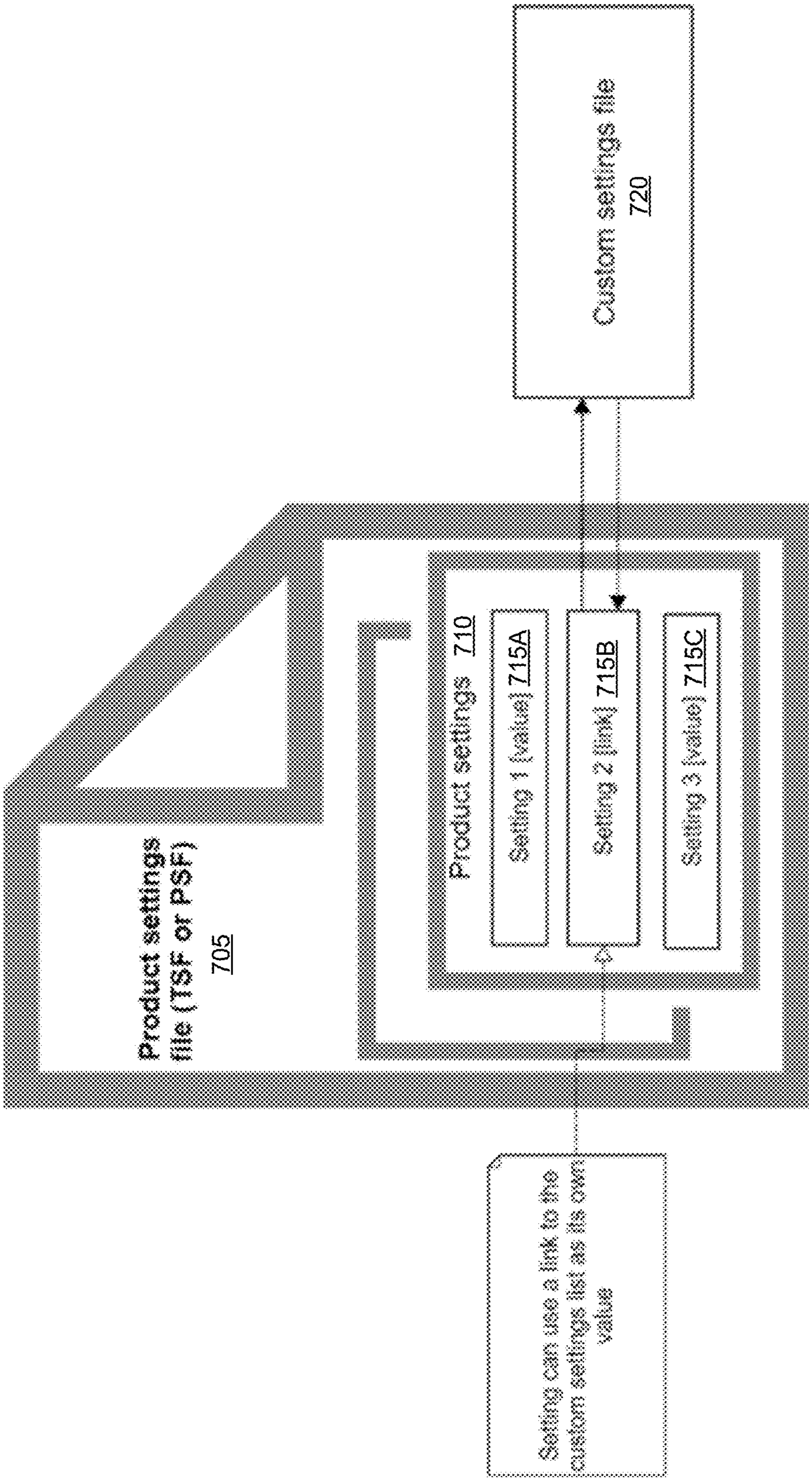
FIG. 7 illustrates an example clinical settings file, in accordance with an embodiment.

FIG. 7 illustrates an example clinical settings file 705, in accordance with an embodiment. In embodiments, product clinical settings files (PSF) and treatment clinical settings files (TSF) are specific for each product type and provide the ability to change each of the settings of a product independently of other products. This allows one to configure the settings of a single product by making changes to the PSF or TSF files for that product. In embodiments, different versions of PSF and/or TSF files may be generated for different doctors, different regions, different patient types, and so on.

Some of the product settings have many parameters (for example tooth movement limits that are represented as a per-tooth table with limits for every corresponding movement). In some embodiments, for such settings there is a mechanism of custom settings. In embodiments, instead of the parameter for the setting itself, the PSF file or other clinical settings file 705 stores a link to a custom settings file 720 with detailed sets of parameters for that setting. When the medical application accesses the setting, it downloads the file with the custom settings and applies settings that this file contains as it does with the other settings. As shown, clinical settings file 705 includes multiple product settings 710 (e.g., clinical settings), which include setting 1 715A that has a set value and setting 3 715C that has a set value. The product settings 710 additionally include setting 2 715B that includes a link to custom settings file 720 rather than including a value or values for the setting 2 715B. Accordingly, when the clinical settings file 705 is loaded, the link for setting 2 715B may be used to access a set or array of clinical settings values for setting 2 715B.

Since the PSF and TSF file set applies only to a certain product, in addition to changing the settings already defined in it, it is also possible to add new settings and even create new products by simply compiling new PSF and TSF files and delivering them to the medical application in embodiments.

Figure 8:
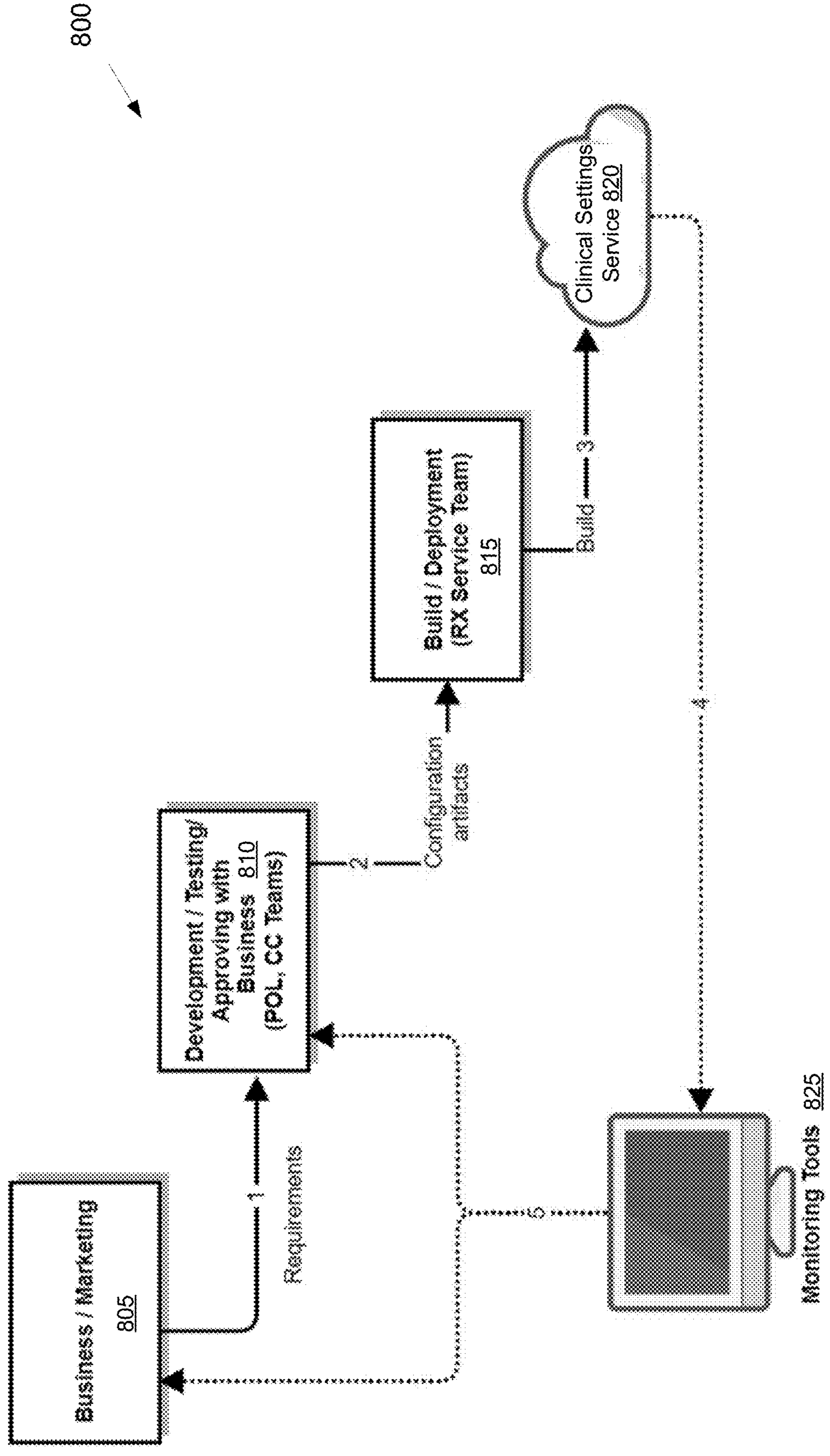
FIG. 8 illustrates a diagram of a procedure for changing product settings of a clinical settings service, in accordance with an embodiment.

FIG. 8 illustrates a diagram of a procedure 800 for changing product settings of a clinical settings service, in accordance with an embodiment.

In some embodiments, two types of changes to a product are defined, including a first type for simple changes and a second type for complex changes. The first type of change is a simple change or set of changes which were already made at least once, and for which possible effects are known or predictable. The second type of change is a complex change, which includes changes that require extensive testing, changes that are made for the first time, and/or any other changes that do not fall under the first type of changes. The procedure for testing the first and second type of changes differs in the presence of additional change validation with the customer and detailed testing of impacted applications in embodiments. For both types of changes the process 800 may include one or more operations, as shown.

A change requestor (e.g., business/marketing team 805) may initiate a request to generate a new product/treatment or to modify an existing product/treatment, and may send the request with one or more requirements for the new or modified product/treatment to a development team 810. The development team 810 may determine one or more properties/parameters for the new or modified product, and may perform one or more tests and/or development with respect to the new or modified product. One or more configuration artifacts specifying the properties/parameters for the new or modified product may be provided to a product service team 815.

The product service team 815 may generate new clinical settings files and/or modify existing clinical settings files, and may perform one or more tests on the new or modified clinical settings files in a test environment. The generated/modified clinical settings files may be deployed to a clinical settings service 820 (and to a production environment) once tests are successfully completed. At each stage of development, one or more monitoring tools 825 may monitor one or more metrics associated with the new or modified product. Such metrics may be monitored, for example, to determine or confirm that changes to a product have a positive effect, for example. In case of any problems with the new clinical settings, an urgent rollback plan may be established to minimize all possible risks from incorrect clinical settings changes delivered to the production environment.

Figure 9:
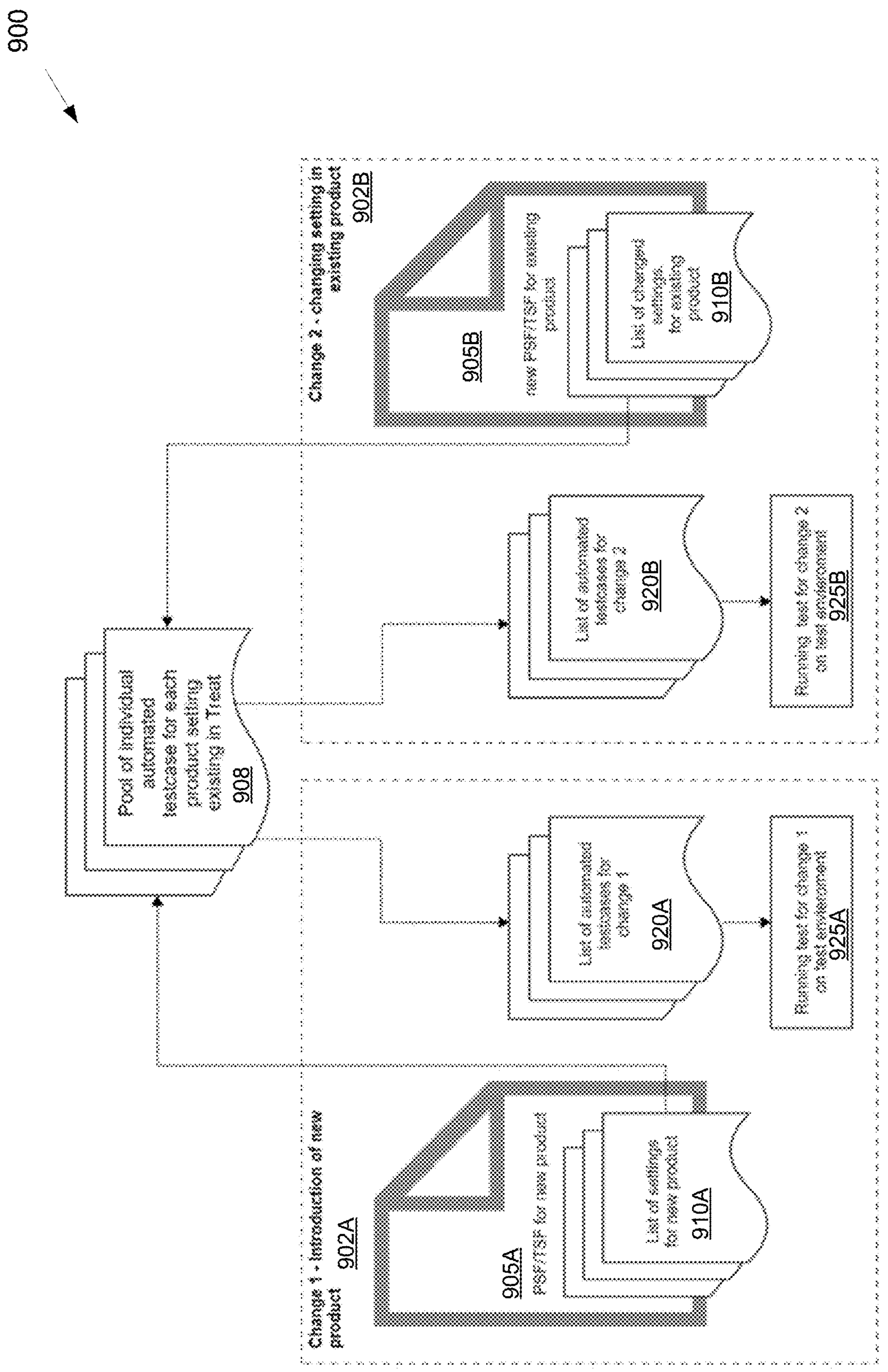
FIG. 9 illustrates a diagram of a procedure for testing changes to clinical settings of a clinical settings service, in accordance with an embodiment.

FIG. 9 illustrates a diagram of a procedure 900 for testing changes to clinical settings of a clinical settings service, in accordance with an embodiment.

For each product setting in the treatment planning software or other medical application, separate automated test scenarios may be prepared. To test a particular product, a list of all included settings for new products may be defined. Alternatively, a list of only changed settings for existing products may be defined. The defined list may be used to run test scenarios for listed settings. In case of a new configuration introduced in the medical application, such a configuration may be covered with separate automated test scenarios so that it can be used for the newly created products.

The test set for the product may be run in a test environment in embodiments. For complex changes, exploratory tests may additionally be performed, as well as user acceptance testing (UAT) and/or smoke tests. After all applied tests are successfully passed, a change can go to the first group of simple changes. Detailed process diagrams are provided for both simple and complex changes.

FIG. 9 illustrates two examples. A first example is for change 1—introduction of new product 902A, which may be initiated by generating new clinical settings files 905A that include a list of clinical settings 910A for the new product. A pool of individual automated test cases 908 may be provided. The pool of individual automated test cases 908 may include tests for each product setting that exists in a medical application. A list 920A of automated tests may be selected from the pool of individual automated test cases 908 based on the clinical settings files 905A. These test cases may be run using clinical settings from the clinical settings files 905A in a test environment at block 925A.

A second example is for change 2—change setting of existing product 902B, which may be initiated by generating new clinical settings files 905B that include a list of clinical settings 910B for the modified product. An example change to the clinical settings file(s) 905B is a change in a maximum permitted number of stages of treatment (e.g., changing from 20 possible stages to 25 possible stages). A list 920B of automated tests may be selected from the pool of individual automated test cases 908 based on the clinical settings files 905B. These testcases may be run using clinical settings from the clinical settings files 905B in a test environment at block 925B.

Figure 10:
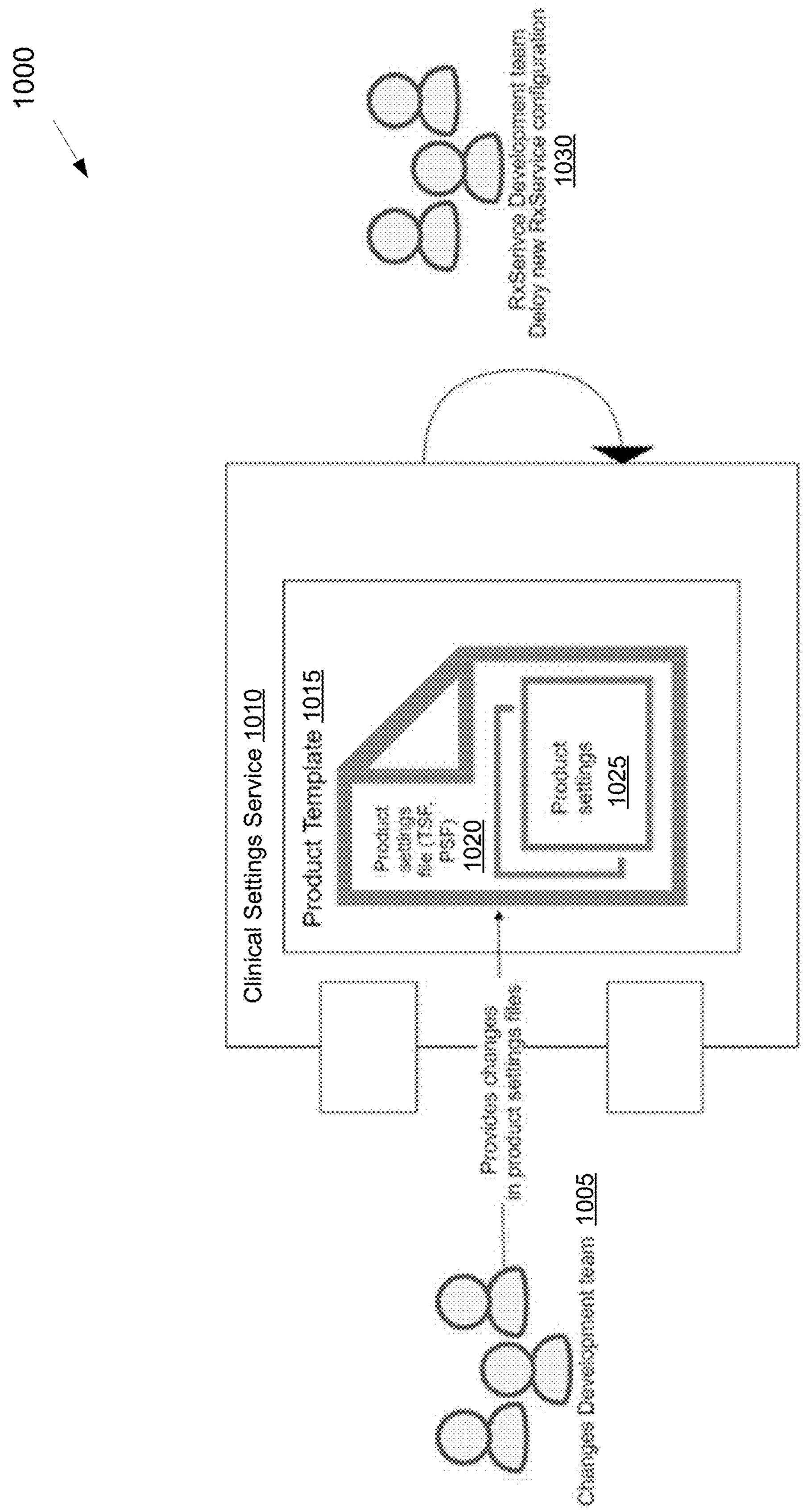
FIG. 10 illustrates a configuration scheme for a clinical settings service, in accordance with an embodiment.

FIG. 10 illustrates a configuration scheme 1000 for a clinical settings service, in accordance with an embodiment.

After making changes to the clinical settings files 1020 (e.g., PSF/TSF files), a changes development team 1005 may provide the changes to an associated product template 1015 in the clinical settings service 1010. In embodiments, the clinical settings service 1010 is a cloud-based application which generates product-specific assets (including clinical settings files such as PSF and TSF files) for each submitted order. The product template 1015 may be generated for each product or treatment that is available in embodiments. Each product template 1015 may include one or more sets of product settings files 1020 (also referred to as clinical settings files), each having one or more product settings 1025. In an example, a product template 1015 may have different product settings files for different doctors, for different regions, for different patient types, and so on. In some embodiments, different product templates 1015 are generated for the same product, but for different countries or regions, for different doctors, and/or for different combinations of regions and doctors.

In embodiments, the assets for the same product can even be different based on certain parameters of a particular treatment case (order treatment type, region, category, patient type, doctor and more). Using these features, it is possible to fine-tune the product settings for a particular region and/or for a particular doctor, for example. In embodiments, a development team 1030 can set the values of most product settings by changing the product configuration template of these settings in the clinical settings service, which makes it possible to be independent of the treatment planning software release cycle.

The clinical settings service 1010 can be configured and deployed with a release cycle that is much shorter than the medical application release cycle in embodiments. This is achieved through the introduction of a standard procedure for making changes to products, and greater (compared with traditional medical applications) flexibility of the clinical settings service itself due to the relatively smaller scale of the activities that are performing for the release of a new configuration version.

Figure 11:
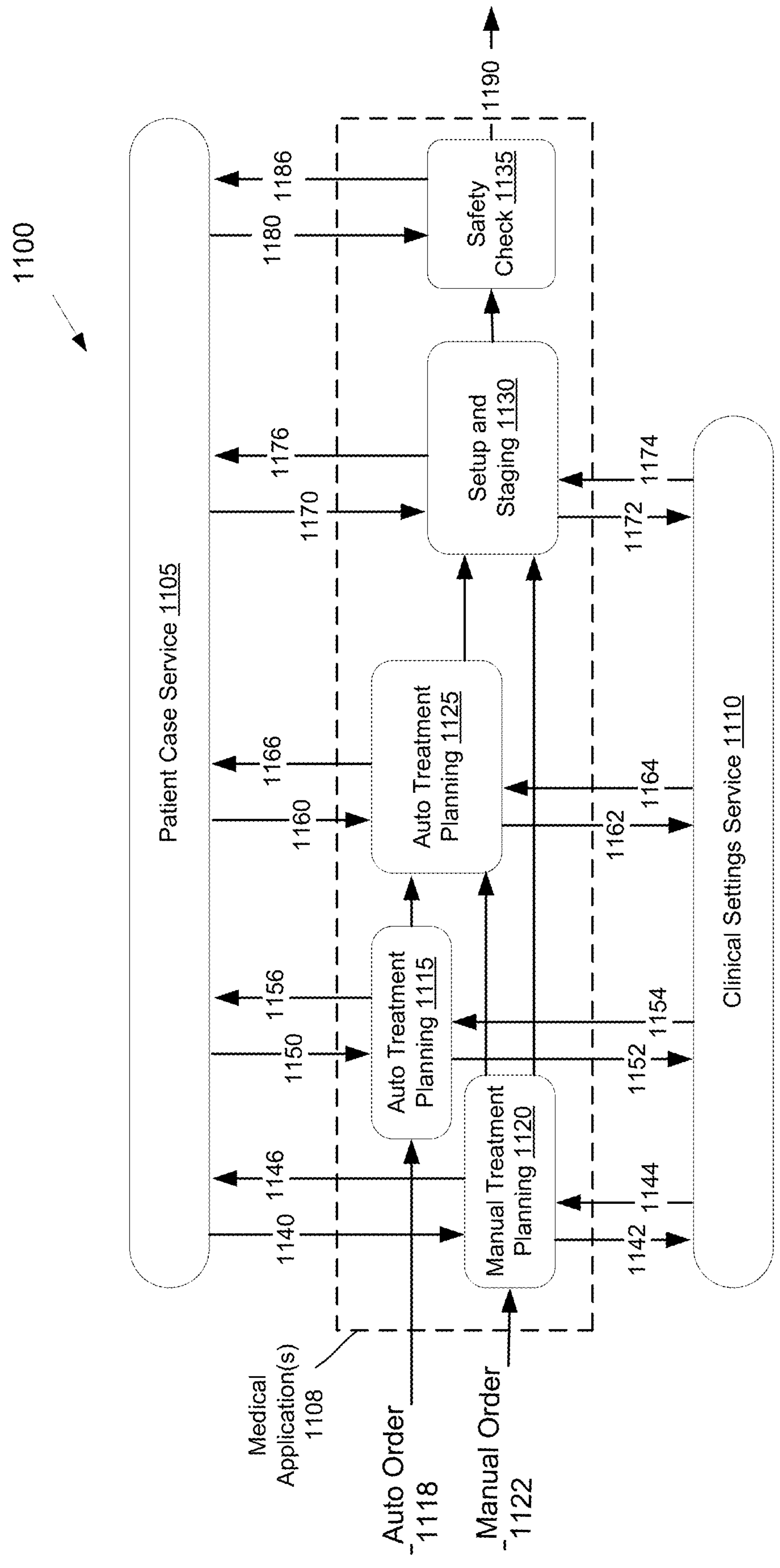
FIG. 11 illustrates a treatment planning scheme for developing a treatment plan using a clinical settings service, in accordance with an embodiment.

FIG. 11 illustrates a treatment planning scheme 1100 for developing a treatment plan using a clinical settings service, in accordance with an embodiment. The treatment planning scheme 1100 may include operations performed by one or more medical applications 1108, a patient case service 1105 and a clinical settings service 1110 in embodiments. In some embodiments, patient case service 1105 is a service that stores patient case records (e.g., patient files, which may include treatment plan files). In some embodiments, patent case service 1105 is a cloud-based service. Clinical settings service 1110 may correspond to any of the clinical settings services described hereinabove. Medical applications 1108 may include one or more medical applications that perform treatment planning. In some embodiments, a doctor (or other user) may load one or more medical applications 1108 and initiate an automated order 1118 to develop a treatment plan or a manual order to develop a treatment plan 1122. In some embodiments, a first medical application is used to implement an automated order 1118 and a second medical application is used to implement a manual order 1122. Alternatively, a same medical application may be used for both automated orders 1118 and manual orders 1122.

Responsive to receiving a manual order 1122 to develop a treatment plan, manual treatment planning 1120 is performed by medical application(s) 1108. This may include sending a request to patient case service 1105 and receiving 1140 a patient case file that lacks clinical settings. For example, when a user (e.g., a CAD designer) opens a patient case in the medical application 1108 (e.g., treatment planning application), the medical application 1108 may download all of that patient case's assets from patient case service 1105 (e.g., using an application programming interface (API) of the patient case service 1105). The patient case file may be loaded into the medical application(s) 1108. The medical application(s) 1108 may send a request 1142 to a clinical settings service 1110 for clinical settings to use for the patient case (e.g., using an API of the clinical settings service 1110), and may receive a response 1144 that includes clinical settings appropriate for the patient case. For example, before, during or after receiving the patient case file, the medical application 1108 may acquire all the clinical settings assets from the clinical settings service 1110 including PSF and TSF files via an API of the clinical settings service 1110. After receiving the clinical settings files, the medical application reads settings values from the clinical settings files (e.g., PSF and/or TSF) and applies them to the patient case (also referred to as a treatment case). A user of the medical application 1108 may then perform one or more manual operations to design a treatment plan, such as designating a final tooth arrangement, designating a number of stages to apply to transition the patient from an initial tooth arrangement to the final tooth arrangement, designating whether to use attachments, and so on. At manual treatment planning 1120, one or more of the treatment planning stages and/or options may be manually configured by a user. Then, after the user finishes processing the patient case and saves it, the medical application 1108 saves all product settings into the a patient case file of the patient case, and sends 1146 the patent case file to patient case service 1105 for storage thereon. Now all downstream applications that open and process the case after the medical application will get the patient case details including the new clinical settings.

The process flow for automatic treatment planning 1115 is similar to the process flow for manual treatment planning 1120. However, automatic treatment planning 1115 is performed in an automated manner by treatment planning software (e.g., by a medical application 1108). Responsive to receiving an auto order 1118 to develop a treatment plan, automatic treatment planning 1115 is performed by medical application(s) 1108. This may include sending a request to patient case service 1105 and receiving 1150 a patient case file that lacks clinical settings. The patient case file may be loaded into the medical application(s) 1108. The medical application(s) 1108 may send a request 1152 to clinical settings service 1110 for clinical settings to use for the patient case, and may receive a response 1154 that includes clinical settings appropriate for the patient case. After receiving the clinical settings files, the medical application reads settings values from the clinical settings files (e.g., PSF and/or TSF) and applies them to the patient case (also referred to as a treatment case). The medical application 1108 then performs one or more operations to automatically generate a treatment plan for the patient case based on the patient case details and the received clinical settings. Then, after the medical application 1108 finishes processing the patient case and saves it, the medical application 1108 saves all product settings into the a patient case file of the patient case, and sends 1156 the patent case file to patient case service 1105 for storage thereon. Now all downstream applications that open and process the case after the medical application will get the patient case details including the new clinical settings.

In some embodiments, a second automatic treatment planning operation (or sequence of operations) 1125 are performed for patient cases. Auto treatment planning 1125 may be similar to auto treatment planning 1115, but may be performed by a more powerful treatment planning application (e.g., medical application 1108) that is a cloud-based service. In some embodiments, auto treatment planning 1125 is performed after auto treatment planning 1115. In some embodiments, auto treatment planning 1125 is performed after manual treatment planning 1120. Alternatively, auto treatment planning 1125 may be skipped after manual treatment planning 1120.

The process flow for automatic treatment planning 1125 is similar to the process flow for automatic treatment planning 1115. However, automatic treatment planning 1125 is performed after manual treatment planning 1120 or auto treatment planning 1115 has already been performed. Accordingly, auto treatment planning 1125 may be triggered after auto treatment planning 1115 or manual treatment planning 1120 are performed. Responsive to such triggering, automatic treatment planning 1125 is performed by medical application(s) 1108. This may include sending a request to patient case service 1105 and receiving 1160 a patient case file. Since the patient case has already been processed at manual treatment planning 1120 or auto treatment planning 1115, the patient case file includes clinical settings. However, clinical settings for a product (e.g., treatment type) to be performed may have changed between when they were accessed during manual treatment planning 1120 or auto treatment planning 1115 and when they are accessed at auto treatment planning 1125. Accordingly, auto treatment planning 1125 may include sending a request 1162 to clinical settings service 1110 for updated clinical settings to use for the patient case, and receiving a response 1164 that includes most recent clinical settings appropriate for the patient case or a notice that the clinical settings have not changed. After receiving the clinical settings files or notice, the medical application reads settings values from the clinical settings files (e.g., PSF and/or TSF), and may replace the clinical settings for the patient case with the newly received clinical settings. If the clinical settings are unchanged, then auto treatment planning 1125 may not include replacement of the clinical settings in the patient case. The medical application 1108 then performs one or more operations to automatically generate a treatment plan for the patient case based on the patient case details and the received clinical settings. Then, after the medical application 1108 finishes processing the patient case and saves it, the medical application 1108 saves all product settings into the patient case file of the patient case, and sends 1166 the patent case file to patient case service 1105 for storage thereon. Now all downstream applications that open and process the case after the medical application will get the updated patient case details including the new clinical settings.

Setup and staging 1130 may be performed after manual treatment planning 1120 and/or after auto treatment planning 1125. Setup and staging 1130 may include determining a number of stages to apply to transition the patient from an initial tooth arrangement to the final tooth arrangement, determining specific tooth movements and/or rotations at individual stages, determining any attachments to apply to teeth and/or which teeth to apply the attachments to and/or at what stages, and so on.

The process flow for setup and staging 1130 is similar to the process flow for automatic treatment planning 1125. Setup and staging 1130 may be triggered after auto treatment planning 1125 or manual treatment planning 1120 are performed. Responsive to such triggering, setup and staging 1130 is performed by medical application(s) 1108. This may include sending a request to patient case service 1105 and receiving 1170 a patient case file. Since the patient case has already been processed at manual treatment planning 1120, auto treatment planning 1115 and/or auto treatment planning 1125, the patient case file includes clinical settings. However, clinical settings for a product (e.g., treatment type) to be performed may have changed between when they were accessed during manual treatment planning 1120 or auto treatment planning 1125 and when they are accessed at setup and staging 1130. Accordingly, setup and staging 1130 may include sending a request 1172 to clinical settings service 1110 for updated clinical settings to use for the patient case, and receiving a response 1174 that includes most recent clinical settings appropriate for the patient case. After receiving the clinical settings files, the medical application reads settings values from the clinical settings files (e.g., PSF and/or TSF), and may replace the clinical settings for the patient case with the newly received clinical settings. If the clinical settings are unchanged, then setup and staging 1130 may not include replacement of the clinical settings in the patient case. The medical application 1108 then performs one or more operations to automatically generate a treatment plan for the patient case based on the patient case details and the received clinical settings. Then, after the medical application 1108 finishes processing the patient case and saves it, the medical application 1108 saves all product settings into the patient case file of the patient case, and sends 1176 the patent case file to patient case service 1105 for storage thereon. Now all downstream applications that open and process the case after the medical application will get the updated patient case details including the new clinical settings.

After setup and staging 1130, one or more final safety checks 1135 may be performed by a medical application 1108 (which may be a different medical application than one that performed manual treatment planning 1120, auto treatment planning 1115, auto treatment planning 1125 and/or setup and staging 1130). A medical application 1108 may retrieve 1180 the patient case file, and load the patient case file. The safety checks that are performed on the patient case may include checks that ensure that patient teeth will not collide during treatment, that forces exceeding force thresholds will not be applied, that teeth will not be moved greater than movement limits, and so on. Once safety checks are performed, a result of the safety checks may be saved to the patient case file, which may be stored 1186 in patient case service 1105. Treatment may then begin at operation 1190. This may include sending instructions to manufacture a set of orthodontic aligners to implement a generated orthodontic treatment plan, for example.

Figure 12:
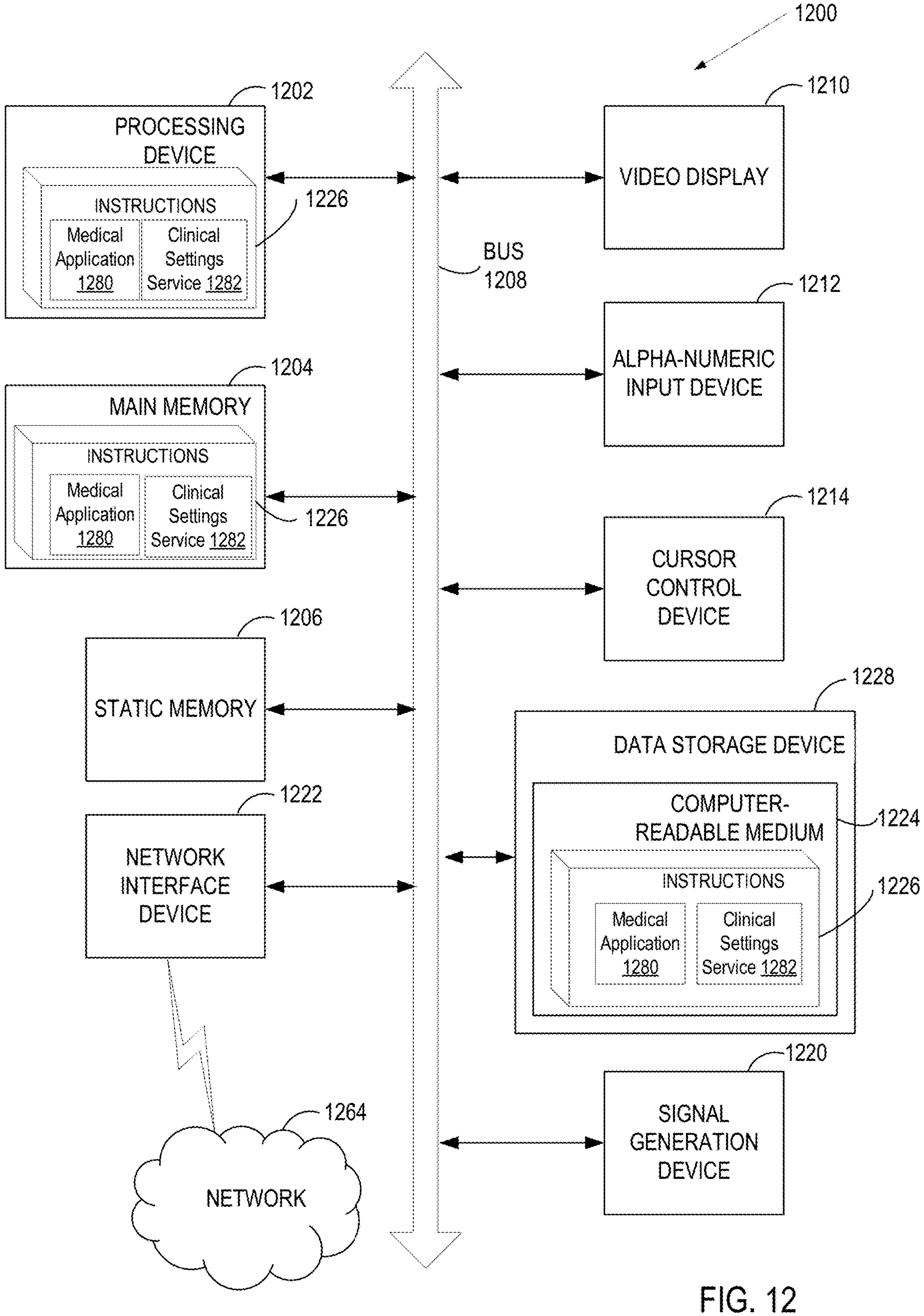
FIG. 12 illustrates a block diagram of an example computing device, in accordance with embodiments of the present disclosure.

FIG. 12 illustrates a diagrammatic representation of a machine in the example form of a computing device 1200 within which a set of instructions, for causing the machine to perform any one or more of the methodologies discussed herein, may be executed. In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a personal digital assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. In one embodiment, the computer device 1200 corresponds to computing device 105 and/or computing device 106 of FIG. 1A.

The example computing device 1200 includes a processing device 1202, a main memory 1204 (e.g., read-only memory (ROM), flash memory, dynamic random access memory (DRAM) such as synchronous DRAM (SDRAM), etc.), a static memory 1206 (e.g., flash memory, static random access memory (SRAM), etc.), and a secondary memory (e.g., a data storage device 1228), which communicate with each other via a bus 1208.

Processing device 1202 represents one or more general-purpose processors such as a microprocessor, central processing unit, or the like. More particularly, the processing device 1202 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 1202 may also be one or more special-purpose processing devices such as an application specific integrated circuit (ASIC), a field programmable gate array (FPGA), a digital signal processor (DSP), network processor, or the like. Processing device 1202 is configured to execute the processing logic (instructions 1226) for performing operations and steps discussed herein.

The computing device 1200 may further include a network interface device 1222 for communicating with a network 1264. The computing device 1200 also may include a video display unit 1210 (e.g., a liquid crystal display (LCD) or a cathode ray tube (CRT)), an alphanumeric input device 1212 (e.g., a keyboard), a cursor control device 1214 (e.g., a mouse), and a signal generation device 1220 (e.g., a speaker).

The data storage device 1228 may include a machine-readable storage medium (or more specifically a non-transitory computer-readable storage medium) 1224 on which is stored one or more sets of instructions 1226 embodying any one or more of the methodologies or functions described herein, such as instructions a medical application 1280 and/or for a clinical settings service 1282. In embodiments, medical application 1280 corresponds to medical application 120 and clinical settings service 1282 corresponds to clinical settings service 116 of FIG. 1A. A non-transitory storage medium refers to a storage medium other than a carrier wave. The instructions 1226 may also reside, completely or at least partially, within the main memory 1204 and/or within the processing device 1202 during execution thereof by the computer device 1200, the main memory 1204 and the processing device 1202 also constituting computer-readable storage media.

The computer-readable storage medium 1224 may also be used to store versions of medical application 1280 and/or to clinical settings service 1282. The computer readable storage medium 1224 may also store a software library containing methods for the medical application 1280 and/or the clinical settings service 1282. While the computer-readable storage medium 1224 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. A system comprising:

a first computing device configured to:

receive, at a clinical settings service executing on the first computing device, a request for clinical settings for a patient case from a medical application executing on a second computing device, wherein the request comprises patient case details;

determine clinical settings for the patient case based at least in part on the patient case details and based on one or more product templates maintained by the clinical settings service, wherein the one or more product templates comprise first clinical settings that are unchangeable by a user of the medical application and second clinical settings that are changeable by the user of the medical application;

determine one or more clinical settings files for the patient case, wherein the one or more clinical settings files comprise a product clinical settings file comprising the first clinical settings that are unchangeable by the user of the medical application and a treatment clinical settings file comprising the second clinical settings that are changeable by the user of the medical application; and send the one or more clinical settings files to the second computing device, wherein the one or more clinical settings files are configured to be read by the medical application to generate a treatment plan for the patient case based on the clinical settings.

2. The system of claim 1, wherein the patient case details comprise at least one of a treatment type, a patient type, a doctor identifier, or a region.

3. The system of claim 2, wherein the treatment type is an orthodontic treatment type, and wherein the clinical settings comprise at least tooth movement settings.

4. The system of claim 1, wherein the one or more clinical settings files are applied by the medical application without redeploying or reinstalling the medical application.

5. The system of claim 1, wherein the first computing device is further configured to:

generate the one or more clinical settings files.

6. The system of claim 1, wherein the product clinical settings file comprises a plurality of clinical settings, wherein for at least one clinical setting of the plurality of clinical settings a link is provided in the product clinical settings file, wherein the link is a link to an additional file that comprises a set of values for the clinical setting.

7. The system of claim 1, wherein the first computing device is further configured to:

receive an instruction to generate a new treatment type, the instruction comprising parameters for clinical settings associated with the new treatment type, prior to receiving the request for clinical settings for the patient case;

wherein the request for clinical settings comprises an indication of the new treatment type, and wherein the new treatment type was unavailable at a time that the medical application was installed on the second computing device.

8. The system of claim 1, wherein the first computing device is further configured to:

receive a request to modify an existing product by applying changes to one or more clinical settings associated with the existing product;

modify the existing product for a test environment;

perform one or more tests for the modified product in the test environment; and responsive to determining that the modified product passes the one or more tests, make the modified product available in a production environment.

9. The system of claim 8, wherein the first computing device is further configured to:

determine whether the changes to the one or more clinical settings have been applied before; and determine what tests to perform based on whether the changes to the one or more clinical settings have been applied before.

10. The system of claim 8, wherein the first computing device is further configured to:

determine that the modified product has caused one or more problems; and revert the modified product to a state that it had before it was modified.

11. The system of claim 1, wherein the medical application is subject to regulatory requirements, and wherein updated approval of the medical application is not required with changes in the clinical settings since changes to the clinical settings do not constitute changes to the medical application.

12. A system comprising:

a first computing device configured to:

open a patient case in a medical application executing on the first computing device;

send, by the first computing device, a request for clinical settings for the patient case to a clinical settings service executing on a second computing device, the request comprising patient case details for the patient case;

receive one or more clinical settings files comprising clinical settings from the clinical settings service, wherein the one or more clinical settings files comprise a product clinical settings file comprising first clinical settings that are unchangeable by a user of the medical application and a treatment clinical settings file comprising second clinical settings that are changeable by the user of the medical application, and wherein the clinical settings are determined by the clinical settings service based at least in part on the patient case details and one or more product templates maintained by the clinical settings service, wherein the one or more product templates comprise the first clinical settings that are unchangeable by the user of the medical application and the second clinical settings that are changeable by the user of the medical application;

read the clinical settings from the one or more clinical settings files;

generate a treatment plan for the patient case, the treatment plan comprising the clinical settings; and store the treatment plan.

13. The system of claim 12, wherein the first computing device is further configured to:

determine a treatment type to be provided for the patient case, wherein the request for clinical settings comprises an identifier of the treatment type.

14. The system of claim 13, wherein support for the treatment type was added after the medical application was installed without redeploying or reinstalling the medical application and without violating regulatory requirements.

15. The system of claim 12, wherein the patient case details comprise at least one of a treatment type, a patient type, a doctor identifier, or a region.

16. The system of claim 15, wherein the treatment type is an orthodontic treatment type, and wherein the clinical settings comprise tooth movement settings.

17. The system of claim 12, wherein the first computing device is further configured to:

apply the clinical settings from the one or more clinical settings files to the patient case by the medical application without redeploying or reinstalling the medical application.

18. The system of claim 12, wherein the product clinical settings file comprises a plurality of clinical settings, wherein for at least one clinical setting of the plurality of clinical settings a link is provided in the product clinical settings file, wherein the link is a link to an additional file that comprises a set of values for the at least one clinical setting, and wherein the one or more clinical settings files comprise the additional file, and wherein the first computing device is further configured to read the set of values for the at least one clinical setting from the additional file.

19. The system of claim 12, wherein the medical application is subject to regulatory requirements, and wherein updated approval of the medical application is not required with changes in the clinical settings since changes to the clinical settings do not constitute changes to the medical application.

* * * * *